(12) United States Patent
Singh et al.

(10) Patent No.: US 6,197,313 B1
(45) Date of Patent: Mar. 6, 2001

(54) RYEGRASS POLLEN ALLERGEN

(75) Inventors: Mohan Bir Singh, Templestowe; Robert Bruce Knox, North Balwyn; Penelope Smith, North Fitzroy; Asil Avjioglu, Doncaster, all of (AU); Piyada Theerakulpisut, Khon Kaen (TH); Terryn Hough, Mordialloc (AU)

(73) Assignee: University of Melbourne, Victoria (AU)

( * ) Notice: Subject to any disclaimer, the term of this patent is extended or adjusted under 35 U.S.C. 154(b) by 0 days.

(21) Appl. No.: 08/434,418

(22) Filed: May 3, 1995

Related U.S. Application Data

(62) Division of application No. 08/413,974, filed on Mar. 31, 1995, which is a continuation of application No. 08/202,861, filed on Feb. 25, 1994, now abandoned, which is a continuation of application No. 07/746,703, filed on Aug. 16, 1991, now abandoned, which is a continuation-in-part of application No. 07/585,086, filed on Oct. 26, 1990, now abandoned.

(30) Foreign Application Priority Data

Mar. 23, 1988 (AU) .................................................... PI7391
Mar. 23, 1989 (WO) .................................. PCT/AU89/00123
Aug. 17, 1990 (AU) .................................................... PK1823

(51) Int. Cl.[7] .................................................. A61K 39/35
(52) U.S. Cl. .................................. 424/275.1; 424/185.1; 424/278.1; 424/93.7; 530/350; 530/370; 514/2; 435/419

(58) Field of Search .............................. 424/185.1–192.1, 424/275.1, 278.1, 93.7; 530/350, 370; 514/2; 435/69.3, 172.3, 419

(56) References Cited

U.S. PATENT DOCUMENTS 4,761,371 * 8/1988 Bell et al. .

OTHER PUBLICATIONS

Esch et al., Molecular Immunology, vol. 26, No. 6, pp. 557–561, 1989.*
Griffith et al., FEBS Letters, vol. 279, No. 2, 210–215, Feb. 1991.*
Perez et al., J. Biol. Chem., vol. 265, No. 27, pp. 16210–16215 (1990).*
Cottam et al., Biochem. J., vol. 234, 305–310 (1986).*
Hatton et al., J. Allergy Immunology, vol. 8(11):183 (1988).*
Stinson et al., 1987, Plant Physiol., vol. 83, p. 442–447.*
Jaye et al. Nucleic Acid Res. 11(8), 1983, p. 2325–2335.*

* cited by examiner

*Primary Examiner*—Laurie Scheiner
(74) *Attorney, Agent, or Firm*—Lahive & Cockfield, LLP; Jane E. Remillard, Esq.; Amy E. Mandragouras, Esq.

(57) ABSTRACT

The present invention provides a nucleic acid sequences coding for the ryegrass pollen allergens Lol pIa and Lol pIb, purified Lol pIa and Lol pIb protein and fragments thereof, methods of producing recombinant Lol pIa and Lol pIb or at least one fragment thereof or derivative or homologue thereof, and methods of using the nucleic acid sequences, proteins and peptides of the invention.

16 Claims, 10 Drawing Sheets

```
                                        CGCTATCCCTCCCTCGTACAAACAAACGCAAGAGCAGCA   39
      -25           -20           -15           -10            -5
    M  A  V  Q  K  Y  T  V  A  L  F  L  R  R  G  P  R  G  G  P  G  R  S  Y  A
ATGGCCGTCCAGAAGTACACGGTGGCTCTATTCCTCCGCCGTGGCCCTCGTGGCGGGCCCGGCCGCTCCTACGCC  114

1             5           10            15            20           25
    A  D  A  G  Y  T  P  A  A  A  A  T  P  A  T  P  A  A  T  P  A  G  G  W  R
GCTGACGCCGGCTACACCCCCGCAGCCGCGGCCACCCCGGCTACTCCTGCTGCCACCCCGGCTGGCGGCTGGAGG  189

26           30            35            40            45
    A  G  D  D  R  R  A  E  A  A  G  G  R  Q  R  L  A  S  R  Q  P  W  P  P
GAAGGCGACGACCGACGAGCAGAAGCTGCTGGAGGACGTCAACGCCTGGCTTCAAGGCAGCCGTGGCCGCCG     261

50             55            60            65            70
    L  P  T  P  L  R  R  T  S  S  R  S  S  R  P  P  S  P  S  P  P  R  A  S  S
CTGCCAACGCCCCTCCGGCGGACAAGTTCAAGATCTTCGAGGCCGCCTTCTCCGAGTCCTCCAAGGGCCTCCTCG  336

75             80            85            90            95
    P  T  S  A  A  K  A  P  G  L  I  P  K  L  D  T  A  Y  D  V  A  Y  K  A  A
CCCACCTCCGCCGCCAAGGCACCCGGCCTCATCCCCAAGCTCGACACCGCCTACGACGTCGCCTACAAGGCCGCC  411

100           105           110           115           120
    E  A  H  P  R  G  Q  V  R  R  L  R  H  C  P  H  R  S  L  R  V  I  A  G  A
GAGGCCCACCCCCGAGGCCAAGTACGACGCCTTCGTCACTGCCCTCACCGAAGCCTCCGCGTCATCGCCGGCGCC  486

125           130           135           140           145
    L  E  V  H  A  V  K  P  A  T  E  E  V  P  A  A  K  I  P  T  G  E  L  Q  I
CTCGAGGTCCACGCCGTCAAGCCCGCCACCGAGGAGGTCCTCGCTGCTAAGATCCCCACCGGTGAGCTGCAGATC  561

150           155           160           165           170
    V  D  K  I  D  A  A  F  K  I  A  A  T  A  A  N  A  A  P  T  N  D  K  F  T
GTTGACAAGATCGATGCTGCCTTCAAGATCGCAGCCACCGCCGCCAACGCCGCCCCCACCAACGATAAGTTCACC  636

175           180           185           190           195
    V  F  E  S  A  F  N  K  A  L  N  E  C  T  G  G  A  M  R  P  T  S  S  S  P
GTCTTCGAGAGTGCCTTCAACAAGGCCCTCAATGAGTGCAGCGGCGGCGCTATGAGACCTACAAGTTCATCCCCT  711

200           205           210           215           220
    P  S  R  P  R  S  S  R  P  T  P  P  P  S  P  A  A  P  E  V  K  Y  A  V  F
CCCTCGAGGCCGCGGTCAAGCAGGCCTACGCCGCCACCGTCGCCCGCCGCGCCCGCGGTCAAGTACGCCGTCTTT  786

225           230           235           240           245
    E  A  A  L  T  K  A  I  T  A  M  T  Q  A  Q  K  A  G  K  P  A  A  A  A  A
GAGGCCGCGCTGACCAAGGCCATCACCGCCATGACCCAGGCACAGAAGGCCGGCAAACCCGCTGCCGCCGCTGCC  861

250           255           260           265           270
    T  A  A  A  T  V  A  T  A  A  A  T  A  A  A  V  L  P  P  P  L  L  V  V  Q
ACAGCGGCCGCAACCGTTGCCACCGCGGCCGCAACCGCCGCCGCCGTGCTGCCACCGCCGCTGCTGGTCGTACAA  936

275           280
    S  L  I  S  L  L  I  Y  Y  *
AGCCTGATCAGCTTGCTAATATACTACTGAACGTATGTAAGTGCATGATCCGGGCGGCGAGTGGTTTTGTTGAT  1010
AATTAATCTTCGTTTTCGTTTTCATGCAGCCGCGATCGAGAGGTTGCATGCTTGTAATAATTCAATATTTTTCA  1064
TTTCTTTTTGAATCTGTAAATCCCCATGACAAGTAGTGGGATCAAGTCGGCATGTATCACCGTTGATGCGAGTT  1158
TAACGATGGGGAGTTTATCAAAGAATTTATTATTAAAAAAAAAAAAAAAAAAAAAAAAAAAAAAAAAA        1232
AAAAAAAAAA                                                                   1242
```

Fig. 3B

```
AC AAT GAG GAG CCT ATC GCA CCC TAC CAC TTC GAC CTC TCG GGC CAC      47
   Asn Glu Glu Pro Ile Ala Pro Tyr His Phe Asp Leu Ser Gly His
    1               5                  10                  15

GCA TTC GGG TCC ATG GCG AAG AAG GGC GAG GAG CAG AAG CTC CGC AGC     95
Ala Phe Gly Ser Met Ala Lys Lys Gly Glu Glu Gln Lys Leu Arg Ser
                 20                  25                  30

GCC GGC GAG CTG GAG CTC CAG TTC AGG CGG GTC AAG TGC AAG TAC CCG    143
Ala Gly Glu Leu Glu Leu Gln Phe Arg Arg Val Lys Cys Lys Tyr Pro
             35                  40                  45

GAC GGC ACC AAG CCG ACA TTC CAC GTC GAG AAG GGT TCC AAC CCC AAC    191
Asp Gly Thr Lys Pro Thr Phe His Val Glu Lys Gly Ser Asn Pro Asn
         50                  55                  60

TAC CTG GCT ATT CTG GTG AAG TAC GTC GAC GGC GAC GGC GAC GTG GTG    239
Tyr Leu Ala Ile Leu Val Lys Tyr Val Asp Gly Asp Gly Asp Val Val
     65                  70                  75

GCC GTG GAC ATC AAG GAG AAG GGC AAG GAT AAG TGG ATC GAG CTC AAG    287
Ala Val Asp Ile Lys Glu Lys Gly Lys Asp Lys Trp Ile Glu Leu Lys
 80                  85                  90                  95

GAG TCG TGG GGA GCA GTC TGG AGG ATC GAC ACC CCC GAT AAG CTG ACG    335
Glu Ser Trp Gly Ala Val Trp Arg Ile Asp Thr Pro Asp Lys Leu Thr
                100                 105                 110

GGC CCA TTC ACC GTC CGC TAC ACC ACC GAG GGC GGC ACC AAA TCC GAA    383
Gly Pro Phe Thr Val Arg Tyr Thr Thr Glu Gly Gly Thr Lys Ser Glu
            115                 120                 125

GTC GAG GAT GTC ATT CCT GAG GGC TGG AAG GCC GAC ACC TCC TAC TCG    431
Val Glu Asp Val Ile Pro Glu Gly Trp Lys Ala Asp Thr Ser Tyr Ser
        130                 135                 140

GCC AAG TGAGCAAGAA GTGGAGTGAT CTTCTTCCAA TCAGCTTAAT TTTGACTCAA      487
Ala Lys
    145

GATCTCAAAT AATCCAGCCG CACATATATA CGAGGCGGTG AGACATACAA GCTCCTCCAT   547

GAGTATATTC ATTCATGCCG TATAGAGAGG AGAAAGATGC CTGAATAAGA GTTTGAGGTC   607

GACACCTTGT GAGAAGTGTA TATAGGAGGA ACCCAATCTG GCTCCATCTT TCTTTGCTCG   667

CACGGTGTAC TGCTAAGGTT ATCTTCTAAC AGGCCAGATT AACCTACTAT CTAATATATG   727

CAACGTATGG TCATTTTCCC TAAAAAAAA                                     756
```

Fig. 6

```
CAAATTCAAG ACAAG ATG GCG TCC TCC TCG TCG GTG CTC CTG GTG GTG GCG         51
              Met Ala Ser Ser Ser Ser Val Leu Leu Val Val Ala
              -23         -20                 -15

CTG TTC GCC GTG TTC CTG GGC AGC GCG CAT GGC ATC GCG AAG GTA CCA          99
Leu Phe Ala Val Pha Leu Gly Ser Ala His Gly Ile Ala Lys Val Pro
    -10             -5                   1                   5

CCG GGC CCC AAC ATC ACG GCC GAG TAC GGC GAC AAG TGG CTG GAC GCG         147
Pro Gly Pro Asn Ile Thr Ala Glu Tyr Gly Asp Lys Trp Leu Asp Ala
                10                  15                  20

AAG AGC ACC TGG TAT GGC AAG CCG ACC GGC GCC GGT CCC AAG GAC AAC         195
Lys Ser Thr Trp Tyr Gly Lys Pro Thr Gly Ala Gly Pro Lys Asp Asn
                25                  30                  35

GGC GGC GCG TGC GGG TAC AAG GAC GTT GAC AAG GCG CCG TTC AAC GGC         243
Gly Gly Ala Cys Gly Tyr Lys Asp Val Asp Lys Ala Pro Phe Asn Gly
            40                  45                  50

ATG ACC GGC TGC GGC AAC ACC CCC ATC TTC AAG GAC GGC CGT GGC TGC         291
Met Thr Gly Cys Gly Asn Thr Pro Ile Phe Lys Asp Gly Arg Gly Cys
        55                  60                  65

GGC TCC TGC TTC GAG ATC AAG TGC ACC AAG CCC GAG TCC TGC TCC GGC         339
Gly Ser Cys Phe Glu Ile Lys Cys Thr Lys Pro Glu Ser Cys Ser Gly
70                  75                  80                  85

GAG GCT GTC ACC GTC ACA ATC ACC GAC GAC AAC GAG GAG CCC ATC GCA         387
Glu Ala Val Thr Val Thr Ile Thr Asp Asp Asn Glu Glu Pro Ile Ala
                90                  95                  100

CCC TAC CAT TTC GAC CTC TCG GGC CAC GCG TTC GGG TCC ATG GCG AAG         435
Pro Tyr His Phe Asp Leu Ser Gly His Ala Pha Gly Ser Met Ala Lys
            105                 110                 115

AAG GGC GAG GAG CAG AAG CTC CGC AGC GCC GGC GAG CTG GAG CTC CAG         483
Lys Gly Glu Glu Gln Lys Leu Arg Ser Ala Gly Glu Leu Glu Leu Gln
        120                 125                 130

TTC AGG CGG GTC AAG TGC AAG TAC CCG GAC GGC ACC AAG CCG ACA TTC         531
Phe Arg Arg Val Lys Cys Lys Tyr Pro Asp Gly Thr Lys Pro Thr Phe
    135                 140                 145

CAC GTC GAG AAG GCT TCC AAC CCC AAC TAC CTC GCT ATT CTG GTG AAG         579
His Val Glu Lys Ala Ser Asn Pro Asn Tyr Leu Ala Ile Leu Val Lys
150                 155                 160                 165

TAC GTC GAC GGC GAC GGT GAC GTG GTG GCG GTG GAC ATC AAG GAG AAG         627
Tyr Val Asp Gly Asp Gly Asp Val Val Ala Val Asp Ile Lys Glu Lys
                170                 175                 180
```

Fig. 7A

```
GGC AAG GAT AAG TGG ATC GAG CTC AAG GAG TCG TGG GGA GCA GTC TGG    675
Gly Lys Asp Lys Trp Ile Glu Leu Lys Glu Ser Trp Gly Ala Val Trp
            185             190             195

AGG ATC GAC ACC CCC GAT AAG CTG ACG GGC CCA TTC ACC GTC CGC TAC    723
Arg Ile Asp Thr Pro Asp Lys Leu Thr Gly Pro Phe Thr Val Arg Tyr
            200             205             210

ACC ACC GAG GGC GGC ACC AAA TCC GAA GTC GAG GAT GTC ATC CCT GAG    711
Thr Thr Glu Gly Gly Thr Lys Ser Glu Val Glu Asp Val Ile Pro Glu
            215             220             225

GGC TGG AAG GCC GAC ACC TCC TAC TCG GCC AAG TGAGCA                 810
Gly Trp Lys Ala Asp Thr Ser Tyr Ser Ala Lys
230             235             240
```

Fig. 7B

RYEGRASS POLLEN ALLERGEN

REFERENCE TO RELATED APPLICATIONS

The present application is a divisional of U.S. Ser. No. 08/413,974 filed on Mar. 31, 1995, which is a file wrapper continuation of U.S. Ser. No. 08/202,861, filed on Feb. 25, 1994, now abandoned, which is a continuation of U.S. Ser. No. 07/746,703, filed Aug. 16, 1991, now abandoned, which is a continuation in part of U.S. Ser. No. 07/585,086, filed Oct. 26, 1990, now abondoned. The disclosures of all of the above-identified cases are hereby incorporated herein by reference.

FIELD OF THE INVENTION

The present invention relates to the major allergenic protein Lol pIb from pollen of ryegrass, *Lolium perenne* L. and to derivatives and homologues thereof and to allergenic proteins immunologically related thereto. The present invention is also directed to recombinant Lol pIa and Lol pIb and their derivatives and to expression vectors capable of directing synthesis of same. Even more particularly, the present invention is directed to cDNA separately encoding Lol pIa and Lol pIb and to expression vectors comprising same.

BACKGROUND OF THE INVENTION

Allergens constitute the most abundant proteins of grass pollen, which is the major cause of allergic disease in temperate climates (Marsh (1975) Allergens and the genetics of allergy; in M. Sela (ed), The Antigens, Vol. 3, pp 271–359, Academic Press Inc., London, New York)., Hill et al. (1979) Medical Journal of Australia 1, 426–429). The first descriptions of the allergenic proteins in ryegrass showed that they are immunochemically distinct, and are known as groups I, II, III and IV (Johnson and March (1965) Nature, 206, 935-; and Johnson and Marsh (1966) Immunochemistry 3, 91–100). Using the International Union of Immunological Societies' (IUIS) nomenclature, these allergens are designated Lol pI, Lol pII, Lol pIII and Lol pIV.

These four proteins have been identified in pollen ryegrass, *Lolium perenne* L., which act as antigens in triggering immediate (Type 1) hypersensitivity in susceptible humans.

Lol pI is defined as an allergen because of its ability to bind to specific IgE in sera of ryegrass-sensitive patients, to act as an antigen in IgG responses and to trigger T-cell responses. The allergenic properties have been assessed by direct skin testing of grass pollen-sensitive patients. The results showed that 84% had a skin sensitivity to Lol pI (Freidhoff et al., (1986) J. Allergy Clin. Immunol. 78:1190–1201) demonstrating the primary importance of this protein as the major allergen. Furthermore, 95% of patients demonstrated to be grass pollen-sensitive possessed specific IgE antibody that bound to Lol pI, as demonstrated by immunoblotting (Ford and Baldo (1986) International Archives of Allergy and Applied Immunology 81:193–203).

Substantial allergenic cross-reactivity between grass pollens has been demonstrated using an IgE-binding assay, the radioallergo-sorbent test (RAST), for example, as described by Marsh et al. (1970) J. Allergy, 46, 107–121, and Lowenstein (1978) Prog. Allergy, 25, 1–62. (Karger, Basel).

The immunochemical relationship of Lol pI with other grass pollen antigens have been demonstrated using both polyclonal and monoclonal antibodies (e.g. Smart and Knox (1979) International Archives of Allergy and Applied Immunology 62:173–187; Singh and Knox (1985) International Archives of Allergy and Applied Immunology 78, 300–304). Antibodies have been prepared to both purified proteins and IgE-binding components. These data demonstrate that the major allergen present in pollen of closely related grasses is immunochemically similar to Lol pI (Singh and Knox, supra).

SUMMARY OF THE INVENTION

In accordance with the present invention, it has been discovered that Lol pI comprises two proteins, designated herein Lol pIa and Lol pIb. The genes encoding these proteins have now been cloned permitting the large scale production of the recombinant allergens. One aspect of the present invention thus provides nucleic acid sequences coding for Lol pIa (SEQ ID NO: 3 and SEQ ID NO: 5) and Lol pIb (SEQ ID NO: 1).

Another aspect of the present invention relates to a recombinant vector comprising a DNA sequence encoding a protein displaying allergenic activity from pollen of a grass species. More particularly, the grass species belongs to the family Poaceae (Gramineae), and even more particularly, to the genus Lolium. Still even more particularly, the allergenic protein in characterized as being immunologically cross-reactive with antibody to Lol pIa or Lol pIb protein of *Lolium perenne* pollen, namely:

Pooid (festucoid) grasses. GROUP 1: Triticanea: *Bromus inermis*, smooth brome; *Agropyron repens*, English couch; *A. cristatum*; *Secale cereale* rye *Triticum aestivum*, wheat. GROUP 2: Poanae: *Dactylis glomerata*, orchard grass of cocksfoot; *Festuca elatior*, meadow fescue; *Lolium perenne*, perennial ryegrass; *L.multiflorum*, Italian ryegrass; *Poa pratensis*, Kentucky bluegrass; *P.compressa*, flattened meadow grass; *Avena sativa*, oat; *Holcus lanatus*, velvet grass or Yorkshire fog; *Anthoxanthum odoratum*; sweet vernal grass; *Arrhenatherum elatius*, oat grass; *Agrostis alba*, red top; *Phleum pratense*, timothy; *Phalaris arundinacea*, reed canary grass. Panicoid grass, *Paspalum notatum*, Bahia grass, Andropogonoid grasses: *Sorghum halepensis*, Johnson grass.

A further aspect of the present invention relates to a recombinant vector comprising a DNA sequence encoding the allergenic protein Lol pIa or Lol pIb of ryegrass, *Lolium perenne*, L. pollen, or derivatives or homologues thereof. More particularly, the present invention relates to a recombinant DNA molecule comprising a eukaryotic or prokaryotic origin of replication, a detectable marker, a DNA sequence encoding either Lol pIa or Lol pIb allergenic protein or derivatives or homologues thereof or an allergenic protein cross-reactive with an antibody to said Lol pIa or Lol pIb protein or their derivatives or homologues and optionally a promoter sequence capable of directing transcription of said allergenic proteins.

Yet another aspect of the present invention contemplates a method for producing recombinant Lol pIa or Lol pIb or derivatives or homologues thereof or an allergenic protein immunologically reactive to antibodies to Lol pIa or Lol pIb or a derivative or homologue thereof, comprising culturing an organism containing a replicable recombinant DNA molecule, said molecule comprising a promoter capable of expression in said organism, the gene encoding Lol pIa or Lol pIb or their derivatives or homologues or an immunologically related protein of Lol pIa or Lol pIb located downstream of and transcribed from said promoter, a selectable marker and a DNA vehicle containing a prokaryotic or eukaryotic origin of replication, under conditions and for a time sufficient for said recombinant DNA molecule to be stably maintained and direct the synthesis of Lol pIa or Lol pIb or their derivatives or homologues.

In yet another aspect of the present invention, there is provided non-native (i.e., recombinant or chemically synthesized) Lol pIa (SEQ ID NO: 5 and SEQ ID NO: 6) or Lol pIb (SEQ ID NO: 1 and SEQ ID NO: 2) or their derivatives or homologues or a non-native allergenic protein immunologically cross-reactive to antibodies to Lol pIa or Lol pIb or their derivatives or homologues.

The Lol pIa and Lol pIb proteins, and fragments or portions derived therefrom (peptides) can be used in methods of diagnosing, treating and preventing allergic reactions to ryegrass pollen.

Still yet another aspect of the present invention relates to antibodies to non-native Lol pIa or Lol pIb or a derivative of homologue thereof.

In still yet another aspect of the present invention, there is provided a method for detecting an antibody to an allergenic protein from pollen of the family Poaceae (Gramineae) in serum or other biological fluid comprising contacting said serum or fluid with recombinant Lol pIa or Lol pIb or their antigenic derivatives for a time and under conditions sufficient for an antibody-Lol-pIa or Lol-pIb complex to form and subjecting said complex to a detecting means.

Another aspect of the present invention relates to a recombinant DNA molecule comprising a ryegrass pollen promoter sequence or homologue or degenerate form thereof located on said molecule and further having one or more restriction sites down stream of said promotor such that a nucleotide sequence inserted into one or more of these sites is transcribable in the correct reading frame.

In one preferred embodiment, the recombinant DNA molecule comprises the promoter directing synthesis of Lol pIa or Lol pIb from pollen of ryegrass, Lolium perenne L. and is thereby a developmentally regulated, pollen specific, expression vector.

A further aspect of the present invention contemplates a method for inducing nuclear male sterility in plants of the family Poaceae comprising the steps of:

a) developing a plant carrying a recombinant DNA molecule comprising a ryegrass pollen promoter sequence or homologue or degenerate form thereof located on said molecule and a nucleotide sequence encoding a polypeptide having a deleterious function in cells derived from the family Poaceae, said nucleotide sequence transcribable from said promoter, and said recombinant DNA molecule stably contained in pollen producing cells, and, b) growing said plants under conditions and for a time sufficient for their developmental stage to cause expression of said nucleotide sequence from said promoter thereby producing the polypeptide having a deleterious function on said pollen producing cells such that pollen formation is inhibited or said pollen is inactive.

Further features of the present invention will be better understood from the following detailed description of the preferred embodiments of the invention in conjunction with the appended figures.

BRIEF DESCRIPTION OF THE FIGURES

FIG. 1a illustrates recognition of a positive clone (12R) by three different MAbs FMC-A1 (40.1), FMC-A7 (12.3), 3.2 (Kahn & Marsh (1986) Molec. Immunol. 23:1281–1288; Singh & Knox (1985) International Archives of Allergy and Applied Immunology 78, 300–304; Smart et al. (1983) International Archives of Allergy and Applied Immunology 72 243–248) and IgE from allergic patients' sera. C is the control in which the primary MAb was omitted. FIG. 1b shows an immunoblot analysis of MAbs and IgE binding to group I antigens from rye-grass pollen. Lane 1 shows total protein profile (Coomassie blue staining); Lane 2: MAb 40.1; Lane 3: MAb 21.3; Lane 4: MAb 12.3; Lane 5: IgE antibodies.

FIG. 2 shows RNA blot hybridization. Poly(A)+ RNAs were isolated from different plant tissues: seed leaf, root and pollen. FIG. 2 shows immunoblot analysis of tissue-type and cell-type specific distribution of group I antigens. The soluble proteins were extracted from different plant tissues: flower, leaf root and pollen, and were immunoblotted using MAbs 40.1, 12.3 and IgE antibodies.

FIGS. 3a, 3b and 3c shows the CDNA sequence (SEQ ID NO: 1), predicted amino acid sequence (SEQ ID NO: 1 and SEQ ID NO: 2) and hydrophilicity profile of rye-grass pollen clone 12R. FIG. 3a shows a schematic restriction map of lambda-12R CDNA. The hatched box represents the predicted translation open reading frame. FIG. 3b shows the nucleotide and deduced amino acid sequence of the 1242 nucleotide EcoRl cDNA insert lambda-12R (SEQ ID NO: 1). The deduced amino acid sequence represented by the single letter code is shown above the DNA sequence in FIG. 3b, and begins at the first potential in-frame initiation codon at nucleotide 40. One uninterrupted open reading frame continues for 308 amino acids (numbered above the DNA sequence in FIG. 3b) and ends with the TGA stop codon denoted by an asterisk. The putative signal peptide is indicated by negative numbers. The amino acid residues 1–9, 12–17, and 19 were identified by N-terminal sequencing. FIG. 3c shows the hydrophilicity profile of predicted amino acid sequence based on method of Hopp and Woods (1981) Proc. Natl Acad. Sci. USA 78:3824–3828, with a window of seven amino acids.

FIG. 4a: IgE antibodies; FIG. 4b, MAb 40.1 and FIG. 4c, MAb 12.3. Controls for FIGS. 4a–c are provided by bacteria transformed with non-recombinant plasmids.

FIG. 5a shows whole pollen grains visualized by scanning electron microscopy, showing the single germinal pore. Scale bar, 30 um. FIG. 5b shows detection of cellular sites of Lol pIa and Lol pIb by immunogold localization—double labelling. FIG. 5c shows the appearance of fresh, viable pollen after exposure to water for 30s, dark field Illumination.

FIG. 6 shows the nucleotide sequence and predicted amino acid sequence of clone 13R which has a sequence coding for part of Lol pIa (SEQ ID No: 3). (The redicted amino acid sequence is also shown in SEQ ID NO: 4).

FIGS. 7a and 7b show the nucleotide sequence of cDNA clone 26.j and its predicted amino acid sequence (SEQ ID NO: 5). (The.predicted amino acid sequence is also shown in SEQ ID NO: 6). Clone 26.j is a PCR-generated, full-length clone of Lol pIa.

DETAILED DESCRIPTION OF THE INVENTION

Figure 1A:
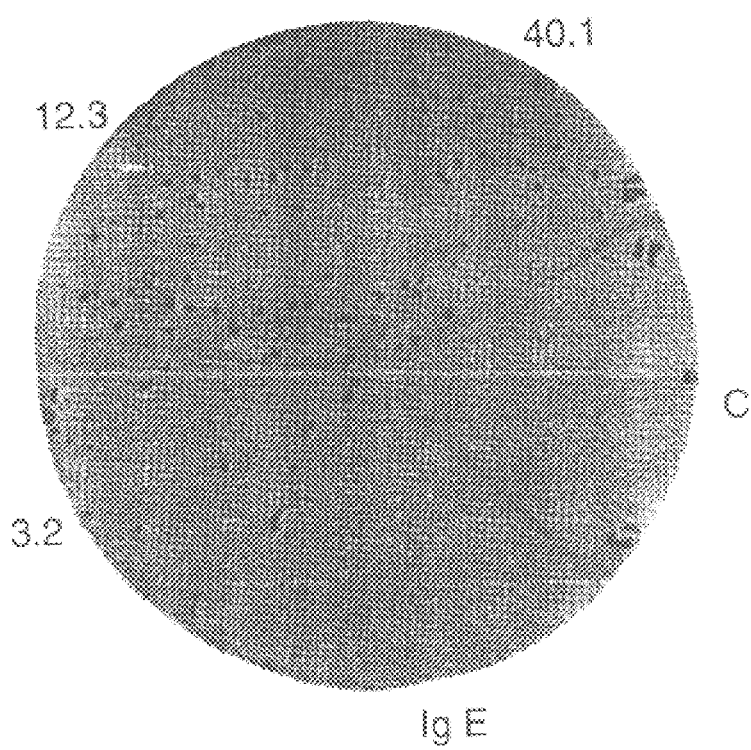
FIGS. 1a and 1b show isolation of cDNA clones specific for the Poaceae Group I allergens.

In accordance with the present invention, there is provided the genes encoding the ryegrass pollen allergens Lol pIa and Lol pIb, a method for expressing same in a host cell, thereby providing a source of recombinant Lol pIa and Lol pIb and the promoter of the Lol pIa and Lol pIb or any genetic sequence placed downstream thereof.

The data herein show that what was considered to be the major allergen of rye-grass pollen, Lol pI, actually comprises two different proteins: Lol pIa, a 35 kD protein, pI 5.5 and Lol pIb, a 31/33 kD protein, pI 9.0. Complementary DNA clones encoding Lol IIa and Lol pIb have been separately isolated and characterized. Lol pIb has a different primary structure and composition from Lol pIa, as deduced from cDNA cloning, $NH_2$-terminal amino acid sequence and the absence of allergenic cross-reactivity. Lol pIb is synthesized in pollen as a preallergen with a 25 amino acid signal peptide which targets the allergen to plastids. This is followed by cleavage of the peptide, and in mature pollen the allergen occurs predominantly in the starch grains.

The original source of the genetic material is fresh ryegrass pollen from *Lolium perenne* L., collected from field sources near Melbourne, Australia and bulk collected pollen from a supplier (Greer Laboratories, Lenoir, N.C.). These sources of pollen are not intended to limit the scope of the invention since they only represent one convenient supply of the pollen. The present invention can be practiced using pollen from any location.

"Gene", is used, in respect of the present invention, in its broadest sense and refers to any contiguous sequence of nucleotides, the transcription of which leads to an mRNA molecule, which mRNA molecule is capable of being translated into a protein. The gene encoding Lol pIa or Lol pIb means the nucleotide sequence encoding the proteins or derivatives or homologues of the proteins which may contain single or multiple amino acid substitutions, deletions or additions including derivatives containing the common antigenic epitope between Lol pIa and Lol pIb. Similarly, in relation to the carbohydrate portion of Lol pIa, derivatives include single or multiple substitutions, deletions or additions to said carbohydrate moiety. The Lol pIa and Lol pIb genes also refer to cDNAs complementary to the mRNAs corresponding to the full or partial length of the Lol pIa and Lol pIb proteins respectively.

It is expected that there are sequence polymorphisms in the nucleic acid sequence coding for Lol pIa and Lol pIb, and it will be appreciated by one skilled in the art that one or more nucleotides in the nucleic acid sequences coding for Lol pIa and Lol pIb may vary among individual *L. perenne* plants due to natural allelic variation. Any and all such nucleotide variations and resulting amino acid polymorphisms are within the scope of the invention. Polymorphisms of the gene coding for Lol pIa discovered during sequencing of the gene are discussed in Example 9. It may also be appreciated by one skilled in the art that Lol pIa and Lol pIb may each be members of separate families of highly related genes whose proteins are present in *L. perenne* pollen (e.g. Rafnar er al. (1991) J. Biol. Chem. 266:1229–1236; Silvanovich et al. (1991) J. Biol. Chem. 266:1204–1210). Nucleotide sequences and corresponding deduced amino acid sequences of any and all such related family members are within the scope of the present invention.

Accordingly, it is within the scope of the present invention to encompass Lol pIa or Lol pIb, at least one fragment (peptide) of Lol pIa or Lol pIb, and their amino acid and/or carbohydrate derivatives and to encompass nucleotide sequences, including DNA, cDNA and mRNA and homologues or degenerate forms thereof, encoding Lol pIa or Lol pIb, said Lol pIa or Lol pIb fragments, or said derivatives thereof. It is further in accordance with the present invention to include molecules such as polypeptides fused to Lol pIa or Lol pIb, or at least one Lol pIa or Lol pIb fragment, or their derivatives or to nucleotide sequences contiguous to Lol pIa or Lol pIb, Lol pIa or Lol pIb fragment, and/or derivative-encoding nucleotide sequences. For example, fof some aspects of the present invention, it is desirable to produce a fusion protein comprising Lol pIa, or Lol pIb or at least one fragment of Lol pIa or Lol pIb, or their derivatives and an amino acid sequence from another peptide or protein, examples of the latter being enzymes such as beta-galactosidase, phosphatase, urease and the like. Most fusion proteins are formed by the expression of a recombinant gene in which two coding sequences have been joined together such that their reading frames are in phase. Alternatively, proteins or peptides can be linked in vitro by chemical means. All such fusion protein or hybrid genetic derivatives of Lol pIa or Lol pIb or their encoding nucleotide sequences are encompassed by the present invention. Furthermore, by homologues and derivatives of Lol pIa or Lol pIb are meant to include synthetic derivatives thereof. The nucleotide sequences as elucidated herein, can be used to chemically synthesize the entire proteins or generate any number of fragments (peptides) by chemical synthesis by well known methods (eg solid phase synthesis). All such chemically synthesized peptides are encompassed by the present invention. Accordingly, the present invention extends to isolated Lol pIa and Lol pIb, fragments thereof and their derivatives, homologues and immunological relatives made by recombinant means or by chemical synthesis and may include derivatives containing the common antigenic epitope between Lol pIa and Lol pIb. The terms isolated and purified are used interchangeably herein and refer to peptides, protein, protein fragments and nucleic acid sequences substantially free of cellular material or culture medium when produced by recombinant DNA techniques, or chemical precursors or other chemicals when synthesized chemically. Furthermore, the present invention extends to proteins or fragments (peptides) corresponding in whole or part to the nucleotide coding sequence given in FIGS. 3*b* (SEQ ID NO: 1), 6 (SEQ ID NO: 3) and 7 (SEQ ID NO: 5), or to degenerate or homologue forms thereof.

Fragments of nucleic acid within the scope of the invention include those coding for parts of Lol pIa or Lol pIb that elicit an antigenic response in mammals, preferably humans, such as the stimulation of minimal amounts of IgE; the eliciting of IgG and IgM antibodies; or the eliciting of a T cell response such as proliferation and/or lymphokine secretion and/or the induction of T cell anergy. The foregoing fragments of Lol pIa or Lol pIb are referred to herein as antigenic fragments. Fragments within the scope of the invention also include those capable of hybridizing with nucleic acid from other plant species for use in screening protocols to detect allergens that are cross-reactive with Lol pIa or Lol pIb. As used herein, a fragment of the nucleic acid sequence coding for Lol pIa or Lol pIb refers to a nucleotide sequence having fewer bases than the nucleotide sequence coding for the entire amino acid sequence of Lol pIa or Lol pIb and/or mature Lol pIa or Lol pIb. Generally, the nucleic acid sequence coding for the fragment or fragments of Lol pIa or Lol pIb will be selected from the bases coding for the mature protein, however, in some instances it may be desirable to select all or a part of a fragment or fragments from the leader sequence portion of the nucleic acid sequence of the invention. The nucleic acid sequence of the invention may also contain linker sequences, restriction endonuclease sites and other sequences useful for cloning, expression or purification of Lol pIa or Lol pIb or fragments thereof.

Fragments of an allergen from ryegrass pollen, preferably Lol pIa or Lol pIb, eliciting a desired antigenic response (referred to herein as antigenic fragments) may be obtained, for example, by screening peptides produced by recombinant methods from the corresponding fragment of the nucleic acid sequence of the invention coding for such peptides or synthesized chemically using techniques known in the art. The peptide fragments of the allergen may be obtained by any method known in the art such as chemical cleavage of the allergen, arbitrary division of the allergen into fragments of a desired length with no overlap of the peptides, or preferably division of the allergen into overlapping fragments of a desired length. The fragments are tested to determine their antigenicity and allergenicity. Fragments of Lol pIa or Lol pIb which are capable of eliciting a T cell response such as stimulation (i.e., proliferation or lymphokine secretion) and/or are capable of inducing T cell anergy are particularly desirable. Fragments of Lol pIa or Lol pIb which do not bind immunoglobulin E (IgE) and/or which have minimal IgE stimulating activity are also desirable. If the fragment or fragments of Lol pIa or Lol pIb bind IgE, it is preferable that such binding does not lead to histamine release, e.g., such binding does not cause cross-linking of IgE on mast cells. Minimal IgE stimulating activity refers to IgE stimulating activity that is less than the amount of IgE production stimulated by the whole Lol pIa or Lol pIb protein. Preferred fragments also include antigenic fragments which, when administered to a ryegrass pollen-sensitive individual, are capable of modifying the allergic response to ryegrass pollen of the individual, and antigenic fragments which, when administered to a ryegrass pollen-sensitive individual, are capable of modifying B-cell response, T-cell response or both B-cell and T-cell response of the individual to a ryegrass pollen antigen.

Screening for IgE binding to the protein or fragments thereof may be performed by scratch tests or intradermal skin tests on laboratory animals or human volunteers, or in in vitro systems such as RAST (radioallergosorbent test), RAST inhibition, ELISA assay or radioimmunoassay (RIA).

The present invention provides expression vectors and host cells transformed to express the nucleic acid sequences of the invention. Nucleic acid coding for Lol pIa or Lol pIb, or at least one fragment thereof may be expressed in bacterial cells such as *E. coli,* insect cells, yeast, or mammalian cells such as Chinese hamster ovary cells (CHO). Suitable expression vectors, promoters, enhancers, and other expression control elements may be found in Sambrook et al. *Molecular Cloning: A Laboratory Manual,* second edition, Cold Spring Harbor Laboratory Press, Cold Spring Harbor, New York, 1989. Expression in yeast, insect or mammalian cells would lead to partial or complete glycosylation of the recombinant material and formation of any inter- or intra-chain disulfide bonds, if such exist. Suitable vectors for expression in yeast include YepSecl (Baldari et al. (1987) Embo J. 6:229–234); pMFα (Kurjan and Herskowitz (1982) Cell 30:933–943); and JRY88 (Schultz et al. (1987) Gene 54:113–123).

For expression in *E. coli,* suitable expression vectors include pTRC (Amann et al. (1988) Gene 69:301–315); pGEX (Amrad Corp., Melbourne, Australia); pMAL (N.E. Biolabs, Beverly, Mass.); pRIT5 (Pharmacia, Piscataway, N.J.); and pSEM (Knapp et al. (1990) BioTechniques 8:280–281). The use of pTRC and pGEX will lead to the expression of unfused protein. The use of pMAL, pRITS and pSEM will lead to the expression of allergen fused to maltose E binding protein (pMAL), protein A (pRIT5), or truncated β-galactosidase (PSEM). When Lol pIa or Lol pIb, fragment, or fragments thereof is expressed as a fusion protein, it is particularly advantageous to introduce an enzymatic cleavage site at the fusion junction between the carrier protein and Lol pIa or Lol pIb or fragment thereof. Lol pIa or Lol pIb or fragment thereof may then be recovered from the fusion protein through enzymatic cleavage at the enzymatic site and biochemical purification using conventional techniques for purification of proteins and peptides. Suitable enzymatic cleavage sites include those for blood clotting Factor X or thrombin for which the appropriate enzymes and protocols for cleavage are commercially available from for example Sigma Chemical Company, St. Louis, Mo. and N.E. Biolabs, Beverly, Mass.

Host cells can be transformed to express the nucleic acid sequences of the invention using conventional techniques such as calcium phosphate or calcium chloride co-precipitation, DEAE-dextran-mediated transfection, or electroporation. Suitable methods for transforming the host cells may be found in Sambrook et al. supra, and other laboratory textbooks. The nucleic acid sequences of the invention may also be synthesized using standard techniques.

Using the structural information now available, it is possible to resign Lol pIa or Lol pIb peptides which, when administered to a ryegrass pollen sensitive individual in sufficient quantities, will modify the individual's allergic response to ryegrass pollen. This can be done, for example, by examining the structure of Lol pIa (SEQ ID NO: 4 or SEQ ID NO: 6) or Lol pIb (SEQ ID NO: 2), producing peptides (via an expression system, synthetically or otherwise) to be examined for their ability to influence B-cell and/or T-cell responses in ryegrass pollen sensitive individuals and selecting appropriate epitopes recognized by the cells. In referring to an epitope, the epitope will be the basic element or smallest unit of recognition by a receptor, particularly immunoglobulins, histocompatibility antigens and T cell receptors where the amino acids essential to the receptor recognition may be contiguous and/or non-contiguous in the amino acid sequence. Amino acid sequences which mimic those of the epitopes and which are capable of down regulating allergic response to Lol pIa or Lol pIb can also be used.

It is now also possible to design an agent or a drug capable of blocking or inhibiting the ability of ryegrass pollen allergen to induce an allergic reaction in ryegrass pollen sensitive individuals. Such agents could be designed, for example, in such a manner that they would bind to relevant anti-Lol pIa or Lol pIb-IgE's, thus preventing IgE-allergen binding and subsequent mast cell degranulation. Alternatively, such agents could bind to cellular components of the immune system, resulting in suppression or desensitization of the allergic response to *L. perenne* pollen allergens. A non-restrictive example of this is the use of appropriate B- and T-cell epitope peptides, or modifications thereof, based on the cDNA/protein structures of the present invention to suppress the allergic response to ryegrass pollen. This can be carried out by defining the structures of B- and T-cell epitope peptides which affect B- and T-cell function in in vitro studies with blood components from ryegrass pollen sensitive individuals.

Protein, peptides or antibodies of the present invention can also be used for detecting and diagnosing ryegrass pollinosis. For example, this could be done by combining blood or blood products obtained from an individual to be assessed for sensitivity to ryegrass pollen with an isolated antigenic peptide or peptides of Lol pIa or Lol pIb, or isolated Lol pIa or Lol pIb protein, under conditions appropriate for binding of components (e.g., antibodies, T-cells, B-cells) in the blood with the peptide(s) or protein and determining the extent to which such binding occurs.

Additionally, sensitivity of a mammal to ryegrass pollen may be determined by administering to a mammal a sufficient quantity of the ryegrass pollen allergen Lol pIa or Lol pIb, or at least one antigenic fragment thereof, produced in a host cell transformed with the nucleic acid sequence of Lol pIa or Lol pIb or fragment thereof or chemically synthesized, to provoke an allergic response in the mammal and determining the occurrence of an allergic response in the mammal to the ryegrass pollen allergen.

The DNA used in any embodiment of this invention can be cDNA obtained as described herein, or alternatively, can be any oligodeoxynucleotide sequence having all or a portion of a sequence represented herein, or their functional equivalents. Such oligodeoxynucleotide sequences can be produced chemically or mechanically, using known techniques. A functional equivalent of an oligonucleotide sequence is one which is 1) a sequence capable of hybridizing to a complementary oligonucleotide to which the sequence (or corresponding sequence portions) of SEQ ID NO: 1), the sequence of SEQ ID NO: 3 or the sequence of SEQ ID NO: 5 or fragments thereof hybridizes, or 2) the sequence (or corresponding sequence portion) complementary to the sequence SEQ ID NO: 1, the sequence of SEQ ID NO: 3, or the sequence of SEQ ID NO: 5 and/or 3) a sequence which encodes a product (e.g., a polypeptide or peptide) having the same functional characteristics of the product encoded by the sequence (or corresponding sequence portion) of SEQ ID NO:1, the sequence of SEQ ID NO: 3 or the sequence of SEQ ID NO: 5. Whether a functional equivalent must meet one or both criteria will depend on its use (e.g., if it is to be used only as an oligoprobe, it need meet only the first or second criteria and if it is to be used to produce a Lol pIa or Lol pIb protein, it need only meet the third criterion).

It is also within the scope of the present invention to include allergenic proteins immunologically cross-reactive with antibodies to Lol pIa or Lol pIb or fragments thereof or their derivatives or homologues and fragments of these allergenic proteins. "Immunologically cross-reactive" is used in its broadest sense and refers generally to a protein capable of detectable binding to an antibody, the latter being specific to Lol pIa or Lol pIb, or to fragments thereof or to derivatives or homologues of Lol pIa or Lol pIb or fragments thereof. Such an immunologically related protein is referred to herein as a immunological relative to Lol pIa or Lol pIb.

Work by others has shown that high doses of allergens generally produce the best results (i.e., best symptom relief). However, many people are unable to tolerate large doses of allergens because of allergic reactions to the allergens. Modification of naturally-occurring allergens can be designed in such a manner that modified peptides or modified allergens which have the same or enhanced therapeutic properties as the corresponding naturally-occurring allergen but have reduced side effects (especially anaphylactic reactions) can be produced. These can be, for example, a protein or peptide of the present invention (e.g., one having all or a portion of the amino acid sequence of Lol pIa or Lol pIb), or a modified protein or peptide, or protein or peptide analogue (e.g., a protein or peptide in which the amino acid sequence has been altered, such as by amino acid substitution, deletion, or addition, to modify immunogenicity and/or reduce allergenicity or to which a component has been added for the same purpose). For example, Lol pIa or Lol pIb protein or peptides can be modified using the polyethylene glycol method of A. Sehon and co-workers. Wie et al. (1981) Int. Arch. Allergy Appl. Immunology. 64:84–99.

Modification of Lol pIa or Lol pIb protein or peptides can also include reduction/alkylation (Tarr [1986] in: Methods of Protein Microcharacterization, J. E. Silver, ed. Humana Press, Clifton, N.J., pp 155–194); acylation (Tarr, supra); esterification (Tarr, supra); chemical coupling to an appropriate carrier (Mishell and Shiigi, eds, [1980] Selected Methods in Cellular Immunology, W. H. Freeman, San Francisco, Calif.; U.S. Pat. No. 4,939,239); or mild formalin treatment (Marsh [1971] Int. Arch. Allergy Appl. Immunol. 41:199–215).

The cloning of the cDNAs encoding Lol pIa and Lol pIb was based on the recognition of the protein expressed by *Escherichia coli* transformed with lambda-gt 11 phage, using both specific monoclonal antibodies and specific serum IgE from grass pollen-sensitive patients. Two such clones are designated 12R and 13R. Also, monoclonal antibodies used were MAbs 3.2, FMC A7 (12.3), 21.3 and FMC A1 (40.1) (Kahn & Marsh (1986) Molec. Immunol. 23:1281–1288; Singh & Knox (1985) International Archives of Allergy and Applied Immunology 78, 300–304; Smart et al. (1983) International Archives of Allergy and Applied Immunology 72 243–248).

Details of the cloning of Lol pIa and Lol pIb are given in the Examples.

The allergenic nature of the subject proteins are characterized in part, by their binding of the reaginic IgE antibodies which are present at high levels in sera of allergic patients. The IgE binding to the epitopes on allergic proteins can be tested in the chromogenic assay in which allergens immobilized on a solid support can be visualized by sequential incubation in (1) allergic patients serum; (2) enzyme-labelled anti-IgE antibodies.

A variety of expression vectors can be constructed for the production of Lol pIa or Lol pIb or their derivatives. Accordingly, another aspect of the present invention contemplates a method of producing recombinant Lol pIa or Lol pIb or at least one fragment of Lol pIa or Lol pIb, or their derivatives or homologues or their immunological relatives (as hereinbefore defined) comprising culturing an organism containing a replicable recombinant DNA molecule, said molecule comprising a promoter capable of expression in said organism, the Lol pIa or Lol pIb gene, at least one fragment of Lol pIa or Lol pIb, or genes encoding their derivatives, homologues or immunological relatives thereof, located downstream of and transcribed from said promoter, a selectable marker and a DNA vehicle containing a prokaryotic or eukaryotic origin of replication, under conditions and for a time sufficient and direct the synthesis of Lol pIa or Lol pIb, at least one fragment of Lol pIa or Lol pIb, or their derivatives, homologues or immunological relatives and then isolating same.

The present invention also extends to the promoter of ryegrass pollen proteins, and particularly, to the promoter of the Lol pIa or Lol pIb gene. This promoter developmentally regulates Lol pIa or Lol pIb gene expression and is organ, i.e., pollen specific. Developmental regulation as, used herein refers to the expression of a particular trait, in this case allergenic proteins in pollen, during a certain stage in a plants life cycle and non-expression during another stage. Hence, the Lol pIa or Lol pIb promoter is particularly useful in allowing expression of Lol pIa or Lol pIb, or any other gene or nucleotide sequence relative thereto, only during the development of pollen. The skilled artisan will immediately recognize the importance of such promoters in selectively expressing a particular trait during pollen formation.

Accordingly, the present invention contemplates a method of inhibiting pollen development or function and thereby inducing nuclear male sterility in plants of the family Poaceae, and in particular *Lolium perenne* L., comprising the steps of:
  a) developing a plant carrying a recombinant DNA molecule comprising the ryegrass pollen promoter sequence or homologue or degenerate form thereof located on said molecule and a nucleotide sequence encoding a polypeptide having a deleterious function in cells derived from the family Poaceae, said nucleotide sequence transcribable from said promoter, and said recombinant DNA molecule stably contained in pollen producing cells, and,
  b) growing said plants under conditions and for a time sufficient for their development stage to cause expression of said nucleotide sequence from said promoter thereby producing the polypeptide having a deleterious function on said pollen producing cells such that pollen formation is inhibited or said pollen is inactive.

Well established methods exist for introducing recombinant DNA molecules into plant cells such as use of Agrobacterium plasmids and electroporation amongst others. By "deleterious function" in respect of a polypeptide refers to a feature of said polypeptide that will inhibit cell growth, cause lysis of a cell, or inhibit various functions in a cell and thereby prevent the normal functioning of the cell. In this case, lethal gene constructs having a deleterious function are contemplated which inhibit or prevent pollen formation and thereby result in a male sterile plant. Such "lethal genes" may encode enzymes, enzyme inhibitors, and/or toxic polypeptides, amongst other molecules. Alternatively, the lethal gene may encode an antisense RNA capable of inhibiting translation of a particular species of mRNA, the translated product thereof, being vital for pollen development.

Male sterile plants are particularly useful in developing hybrid crop varieties.

The Lol pIa or Lol pIb promoter is isolatable from ryegrass genomic DNA by any number of procedures including use of promoter probes vectors, "chromosome walking" and S1 nuclease mapping and sequencing as DNA upstream of the transcription initiation site.

Accordingly, the present invention contemplates a recombinant DNA molecule comprising a ryegrass pollen promoter sequence, and in particular the promoter for the Lol pIa or Lol pIb gene, or homologues or degenerate forms thereof located on said molecule and further having one or more restriction endonuclease sites downstream of said promoter such that nucleotide sequence inserted into one or more of these sites is transcribable in the correct reading frame. As used herein, the "correct reading frame" has the same meaning as "in phase". The aforementioned DNA molecule will preferably also have a selectable marker thereon, such as an antibiotic or other drug resistance gene, such as for example gene encoding resistance to ampicillin, carbenicillin, tetracycline, streptomycin and the like. The recombinant molecule will further comprise a means for stable inheritance in a prokaryotic and/or eukaryotic cell. This can be accomplished by said recombinant molecule carrying a eukaryotic and/or a prokaryotic origin of replication as hereinbefore described in relation to expression vectors.

Alternatively, the recombinant molecule will carry a means for integration into a host cell genome thereby permitting replication of said recombinant molecule in synchrony with the replication of said host cell genome. Examples of preferred prokaryotic hosts include cells *E. coli*, Bacillus and Pseudomonas amongst others. Preferred eukaryotic hosts include cells from yeast and fungi, insects, mammals and plants. Even more preferred host cells are plants of the family Poaceae, and in particular of the genus Lolium, such as *Lolium perenne*. Accordingly in a preferred embodiment, the Lol pIa or Lol pIb gene promoter with a gene encoding a deleterious function positioned relative thereto will be carried by a recombinant DNA molecule capable of integration into the genome of cells of plants from the family Poaceae, or *perenne*. Such a recombinant DNA molecule is transferred to the aforementioned cells by, for example, electroporation. Ideally, said cells are callus-derived cells. Said callus-derived cells transformed with said recombinant DNA molecule are then permitted to regenerate into whole plants. Whole plants entering the pollen of the Lol pIa or Lol pIb gene promoter and, hence, expression of the gene encoding a deleterious function. Consequently, pollen development is inhibited or prevented and a nuclear male sterile plant results therefrom.

Alternatively, the Lol pIa or Lol pIb promoter will direct expression of a gene having advantageous functions, such as a cytokinin. All such recombinant DNA molecules are encompassed by the present invention.

The present invention extends to monoclonal and polyclonal antibodies to recombinant or chemically synthesized Lol pIa or Lol pIb, or at least one fragment of Lol pIa or Lol pIb, produced according to the methods described in International Patent Application No. PCT/AU89/00123 and to their use in immunoassays and test kits as described therein.

The monoclonal antibodies used in the present work to screen the cDNA library for Lol pIa clones showed cross-reactivity with allergenic proteins from pollen of various related grass species. This shows there is a homology between allergenic proteins produced by these pollens with Lol pI allergen supporting the applicability of the present invention to all related grasses. The present invention also relates to antibodies to recombinant Lol pIa or Lol pIb, their derivatives, homologues and immunological relatives including their chemical synthetic derivatives. In the following discussion, reference to Lol pIa or Lol pIb includes their derivatives, homologues and immunological relatives and chemical synthetic derivatives thereof. Such antibodies are contemplated to be useful in developing detection assays (immunoassays) for said Lol pIa or Lol pIb especially during the monitoring of a therapeutic or diagnostic regimen and in the purification of Lol pIa or Lol pIb. The antibodies may be monoclonal or polyclonal. Additionally, it is within the scope of this invention to include any second antibodies (monoclonal or polyclonal) directed to the first antibodies discussed above. The present invention further contemplates use of these first or second antibodies in detection assays and, for example, in monitoring the effect of a diagnostic or an administered pharmaceutical preparation. Furthermore, it is within the scope of the present invention to include antibodies to the glycosylated regions of Lol pIa (where present), and to any molecules complexed with said Lol pIa. Accordingly, an antibody to Lol pIa or Lol pIb encompasses antibodies to Lol pIa or Lol pIb, or antigenic parts thereof, and to any associated molecules (e.g., glycosylated regions, lipid regions, carrier molecules, fused proteins, and the like).

The Lol pIa or Lol pIb, or parts thereof, considered herein are purified then utilized in antibody production. Both polyclonal and monoclonal antibodies are obtainable by immunization with Lol pIa or Lol pIb, and either type is utilizable for immunoassays. The methods of obtaining both types of sere are well known in the art. Polyclonal sera are less preferred but are relatively easily prepared by injection of a suitable laboratory animal with an effective amount of the purified Lol pIa or Lol pIb, or antigenic parts thereof, collecting serum from the animal, and isolating specific sera by any of the known immunoadsorbent techniques. Although antibodies produced by this method are utilizable in virtually any type of immunoassay, they are generally less favored because of the potential heterogeneity of the product.

The use of monoclonal antibodies in an immunoassay is particularly preferred because of the ability to produce them in large quantities and the homogeneity of the product. The preparation of hybridoma cell lines for monoclonal antibody production derived by fusing an immortal cell line and lymphocytes sensitized against the immunogenic preparation can be done by techniques which are well known to those who are skilled in the art. (See, for example, Kohler and Milstein (1975) Nature 256:495–497 and Kohler and Milstein (1986) Eur J. Immunol. 6:511–119).

Unlike preparation of polyclonal sera, the choice of animal is dependent on the availability of appropriate immortal lines capable of fusing with lymphocytes. Mouse and rat have been the animals of choice in hybridoma technology and are preferably used. Humans can also be utilized as sources for sensitized lymphocytes if appropriate immortalized human (or nonhuman) cell lines are available. For the purpose of the present invention, the animal of choice may be injected with from about 0.1 mg to about 20 mg of the purified Lol pIa or Lol pIb, or parts thereof. Usually the injecting material is emulsified in Freund's complete adjuvant. Boosting injections may also be required. The detection of antibody production can be carried out by testing the antisera with appropriately labelled antigen. Lymphocytes can be obtained by removing the spleen or lymph nodes of sensitized animals in a sterile fashion and carrying out fusion. Alternatively, lymphocytes can be stimulated or immunized in vitro, as described, for example, in Reading (1982) J. Immunol. Methods 53:261–291).

A number of cell lines suitable for fusion have been developed, and the choice of any particular line for hybridization protocols is directed by any one of a number of criteria such as speed, uniformity of growth characteristics, deficiency of its metabolism for a component of the growth medium, and potential for good fusion frequency.

Intraspecies hybrids, particularly between like strains, work better than interspecies fusions. Several cell lines are available, including mutants selected for the loss of ability to secrete myeloma immunoglobin.

Cell fusion can be induced either by virus, such as Epstein-Barr or Sendai virus, or polyethylene glycol. Polyethylene glycol (PEG) is the most efficacious agent for the fusion of mammalian somatic cells. PEG itself may be toxic for cells, and various concentrations should be tested for effects on viability before attempting fusion. The molecular weight range of PEG may be varied from 1000 to 6000. It gives best results when diluted to from about 20% to about 70% (w/w) in saline or serum-free medium. Exposure to PEG at 37° C. for about 30 seconds is preferred in the present case, utilizing murine cells. Extremes of temperature (i.e., about 45° C.) are avoided, and preincubation of each component of the fusion system at 37° C. prior to fusion can be useful. The ratio between lymphocytes and malignant cells is optimized to avoid cell fusion among spleen cells and a range of from about 1:1 to about 1:10 is commonly used.

The successfully fused cells can be separated from the myeloma line by any technique known by the art. The most common and preferred method is to chose a malignant line which is hypoxanthine Guanine Phosphoribosyl Transferae (HGPRT) deficient, which will not grow in an aminopterin-containing medium used to allow only growth of hybrids, and aminopterin-containing medium used to allow only growth of hybrids and which is generally composed of hypoxanthine $1.10^{-4}M$, aminopterin $1\times10^{-5}M$, and thymidine $3\times10^{-5}M$, commonly known as the HAT medium. The fusion mixture can be grown in the HAT-containing culture medium immediately after the fusion or 24 hours later. The feeding schedules usually entail maintenance in HAT medium for two weeks and then feeding with either regular culture medium or hypoxanthine, thymidine-containing medium.

The growing colonies are then tested for the presence of antibodies that recognize the antigenic preparation. Detection of hybridoma antibodies can be performed using an assay where the antigen is bound to a solid support and allowed to react to hybridoma supernatants containing putative antibodies. The presence of antibodies may be detected by "sandwich" techniques using a variety of indicators. Most of the common methods are sufficiently sensitive for use in the range of antibody concentrations secreted during hybrid growth.

Cloning of hybrids can be carried out after 21–23 days of cell growth in selected medium. Cloning can be preformed by cell limiting dilution in fluid phase or by directly selecting single cells growing in semi-solid agarose. For limiting dilution, cell suspensions are diluted serially to yield a statistical probability of having only one cell per well. For the agarose technique, hybrids are seeded in a semisolid upper layer, over a lower layer containing feeder cells. The colonies from the upper layer may be picked up and eventually transferred to wells.

Antibody-secreting hybrids can be grown in various tissue culture flasks, yielding supernatants with variable concentrations of antibodies. In order to obtain higher concentrations, hybrids may be transferred into animals to obtain inflammatory ascites. Antibody-containing ascites can be harvested 8–12 days after intraperitoneal injection. The ascites contain a higher concentration of antibodies but include both monoclonals and immunglobulins from the inflammatory ascites. Antibody purification may then be achieved by, for example, affinity chromatography.

The presence of Lol pIa or Lol pIb contemplated herein, or antibodies specific for same, in a patient's serum, plant or mammalian tissue or tissue extract, can be detected utilizing Antibodies prepared as above, either monoclonal or polyclonal, in virtually any type of immunoassay. A wide range of immunoassay techniques are available as can be seen by reference to U.S. Pat. Nos. 4,015,043, 4,424,279 and 4,018,653. This, of course, includes both single-site and two-site, or "sandwich", assays of the non-competitive types, as well as in the traditional competitive binding assays. Sandwich assays are among the most useful and commonly used assays and are favored for use in the present invention. A number of variations of the sandwich assay technique exist, and all are intended to be encompassed by the present invention. Briefly, in a typical forward assay, an unlabelled antibody is immobilized in a solid substrate and the sample to be tested brought into contact with the bound molecule. After a suitable period of incubation, for a period of time sufficient to allow formation of an antibody-antigen secondary complex, a second antibody, labelled with a reporter molecule capable of producing a detectable signal is then added and incubated, allowing time sufficient for the formation of a tertiary complex of antibody-antigen-labelled antibody (e.g., antibody-Lol pia-antibody or antibody-Lol pIb-antibody). Any unreacted material is washed away, and the presence of the antigen is determined by observation of a signal produced by the reporter molecule. The results may either be qualitative, by simple observation of the visible signal, or may be quantitated by comparing with a control sample containing known amounts of hapten. Variations on the forward assay include a simultaneous assay, in which both sample and labelled antibody are added simultaneously to the bound antibody, or a reverse assay in which the labelled antibody and sample to be tested are first combined, incubated and then added simultaneously to the bound antibody. These techniques are well known to those skilled in the art, including any minor variations as will be readily apparent.

Although the following discussion is concerned with detecting Lol pIa or Lol pIb, it is equally applicable to detecting antibodies to Lol pIa or Lol pIb and it is intended to be sufficient description thereof. In the typical forward sandwich assay, a first antibody having specificity for Lol pIa or Lol pIb, or antigenic parts thereof, contemplated in this invention, is either covalently or passively bound to a solid surface. The solid surface is typically glass or a polymer, the most commonly used polymers being cellulose, polyacrylamide, nylon, polystyrene, polyvinyl chloride or polypropylene. The solid supports may be in the form of tubes, beads, discs of microplates, or any other surface suitable for conducting an immunoassay. The binding processes are well-known in the art and generally consist of cross-linking covalently binding or physically adsorbing, the polymer-antibody complex is washed in preparation for the test sample. An aliquot of the sample to be tested is then added to the solid phase complex and incubated at 25° C. for a period of time sufficient to allow binding of any subunit present in the antibody. The incubation period will vary but will generally be in the range of about 2–40 minutes. Following the incubation period, the antibody subunit solid phase is washed and dried and incubated with a second antibody specific for a portion of the hapten. The second antibody is linked to a reporter molecule which is used to indicate the binding of the second antibody to the hapten.

By "reporter molecule," as used in the present specification, is meant a molecule which, by its chemical nature, provides an analytically identifiable signal which allows the detection of antigen-bound antibody. Detection may be either qualitative or quantitative. The most commonly used reporter molecules in this type of assay are either enzymes, fluorophores or radionuclide containing molecules (i.e., radioisotopes). In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, beta-galactosidase and alkaline phosphatase, amongst others. The substrates to be used with the specific enzymes are generally chose for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine, 5-aminosalicylic acid, or toluidine are commonly used. It is also possible to employ fluorogenic substrates, which yield a fluorescent product rather than the chromogenic substrates noted above. In all cases, the enzyme-labelled antibody is added to the first antibody hapten complex, allowed to bind, and then the excess reagent is washed away. A solution containing the appropriate substrate is then added to the tertiary complex of antibody-antigen-antibody. The substrate will react with the enzyme linked to the second antibody, giving a qualitative visual signal, which may be further quantitated, usually spectrophotometrically, to give an indication of the amount of hapten which was present in the sample. "Reporter molecule" also extends to use of cell agglutination or inhibition of agglutination such as red blood cells or latex beads, and the like.

Alternately, fluorescent compounds, such as fluorescein and rhodamine, may be chemically coupled to antibodies without altering their binding capacity. When activated by illumination with light of a particular wavelength, the fluorochrome-labelled antibody adsorbs the light energy, inducing a state of excitability in the molecule, followed by emission of the light at a characteristic color visually detectable with a light microscope. As in the EIA, the fluorescent labelled antibody is allowed to bind to the first antibody-hapten complex. After washing off the unbound reagent, the remaining tertiary complex is then exposed to the light of the appropriate wavelength, the fluorescein observed indicates the presence of the hapten of interest. Immunofluorescence and EIA techniques are both very well established in the art and are particularly preferred for the present method. However, other reporter molecules, such as radioisotope, chemilluminescent or bioluminescent molecules, may also be employed. It will be readily apparent to the skilled technician how to vary the procedure to suit the required purpose. It will also be apparent that the foregoing can be used to detect directly or indirectly (i.e., via antibodies) the Lol pIa or Lol pIb protein of this invention.

Accordingly, one aspect of the present invention contemplates a method of detecting Lol pIa or Lol pIb or a derivative or homologue thereof or a allergenic protein immunologically reactive with said Lol pIa or Lol pIb or their derivative or homologue in serum, tissue extract, plant extract or other biologically fluid comprising the steps of containing said serum, extract or fluid to be tested with ap antibody to Lol pIa or Lol pIb for a time and under conditions sufficient for an allergenic protein-antibody complex to form and subjecting said complex to a detecting means. The present invention also contemplates a method of detecting an antibody to an allergenic protein from pollen of the family Poaceae (Gramineae) in serum or other biological fluid comprising contacting said serum or fluid with recombinant Lol pIa or Lol pIb or their antigenic derivative for a time and under conditions sufficient for an antibody-Lol pIa or Lol pIb complex to form and subjecting said complex to a detecting means. The latter complex may be detected by the Lol pIa or Lol pIb having attached thereto a reporter molecule or by addition of a second antibody labelled with a reporter molecule.

Accordingly, the present invention is also directed to a kit for the rapid and convenient assay for antibodies to Lol pIa or Lol pIb or their derivatives, homologues or immunological relatives in mammalian body fluids (e.g., serum, tissue extracts, tissue fluids), in vitro cell culture supernatants, and cell lysates. The kit is compartmentalized to receive a first container adapted to an antigenic component thereof, and a second container adapted to contain an antibody to Lol pIa or Lol pIb said antibody being labelled with a reporter molecule capable of giving a detectable signal as hereinbefore described. If the reporter molecule is an enzyme, then a third container adapted to contain a substrate for said enzyme is provided. In an exemplified use of the subject kit, a sample to be tested is contacted to the contents of the first container for a time and under conditions for an antibody, if present, to bind to Lol pIa or Lol pIb in said first container. If Lol pIa or Lol pIb of the first container has bound to antibodies in the test fluid, the antibodies of the second container will bind to the secondary complex to form a tertiary complex and, since these antibodies are labelled with a reporter molecule, when subjected to a detecting means, the tertiary complex is detected. Therefore, one aspect of the present invention is a kit for the detection of antibodies to a protein having allergenic properties, said protein from pollen of the family Poaceae (Gramineae), the kit being compartmentalized to receive a first container adapted to contain recombinant Lol pIa or Lol pIb or their antigenic derivative or homologue, and a second container adapted to contain and antibody to Lol pIa or Lol pIb or their derivative or homologue, said antibody labelled with a reporter molecule capable of giving a detectable signal. The "report molecule" may also involve agglutination of red blood cells (RBC) on latex beads. In this kit the reporter molecule is a radioisotope, an enzyme, a fluorescent molecule, a chemilluminescent molecule, bioluminescent molecule or RBC. The kit alternatively comprises a container adapted to contain recombinant Lol pIa or Lol pIb or their antigenic derivative or homologue labelled with a reporter molecule capable of giving a detectable signal.

Because of the presence of allergens in the environment, hayfever and seasonal asthma continue to have significant morbidity and socio-economic impact on Western communities, despite advances made in their pharmacology and immunology. While the available spectrum of drugs, including anti-histamines and steroids have resulted in improvement in the treatment of allergic disease, they have unfortunate side-effects associated with longterm usage. Because of these problems, renewed interest has been shown in the immunotherapy of allergic disease. Immunotherapy involves the injection of potent allergen extracts to desensitize patents against allergic reactions (Bousquet and Michel (1989) Allergy Clin. Immunol. News 1:7–10). Unfortunately, the pollen preparations used as allergens are polyvalent and of poor quality. Consequently, concentrations used are frequently high in order to induce IgG responses, but may be lethal through triggering of systemic reactions, including anaphylaxis. The cloned gene product or synthetic peptides based on the sequence of allergens provides a safer medium for therapy since it can be quality controlled, characterized and standardized.

The precise mechanism for symptomatic relief remains hypothetical. However, administration of a preparation comprising the protein or at least one fragment thereof of the instant invention to a ryegrass-sensitive individual will modify the allergic response of a ryegrass-sensitive individual to ryegrass pollen allergens, e.g., by modifying the B-cell response to Lol pIa or Lol pIb, the T-cell response to Lol pIa or Lol pIb, or both responses.

Currently immunotherapy is one of the most frequently administered treatments in allergology, and in the USA it is considered the first choice. An advantage of this treatment for pollen rhinitis is that treatment takes up to 3 years, while pharmacotherapy must be carried out during the patent's entire life time. Patients given pollen extract for immunotherapy showed a clinical benefit that lasted for four years after the end of treatment (Grammer et al. (1984) J. Allergy Clin. Immunol. 73:484–489).

Immune responsiveness to rye-grass pollen allergens Lol pII and Lol pIII in the human population is significantly associated with the histocompatibility leukocyte antigen HLA-DR3 (Friedhoff et al.(1988) Tissue Antigens 31:211–219; Ansari, et al. (1989) Human Immunol. 25:59–71; Ansari et al. (1989) Int Arch. Allergy Appl. Immunol. 88:164–169). This means that the HLA-DR3 encoded class II Ia molecules of the antigen-presenting cells may recognize a similar immunodominant T cell/Ia recognition site present on another allergen. Lol pIa is known to share an immunodominant T cell/Ia recognition site (YTTEGGTKS EVEDV IP) with both Lol pII and Lol pIII (Friedhoff et al., supra). Most allergic individuals who respond to Lol pII and III also respond to Lol pI, but not the reciprocal. Thus, Lol pIa appears to have unique T cell/Ia recognition site(s) not present in Lol pII or III. These unique site(s) appear to be common between Lol pIa and Lol pIb. Certainly, the common T cell/Ia recognition site shared between Lol pIa, II and III is not represented in the deduced sequence of Lol pIb.

Furthermore, it is demonstrated herein that Lol pIa and Lol pIb possess a common B-cell epitope, present in fragment 2P. This common epitope has bene detected using all three MAbs reactive with Lol pIa. This represents an epitope that is common between Lol pIa and Lol pIb, but not present in Lol pII and III, and is likely to be responsible for the demonstrated concordant responsiveness.

Accordingly, the present invention is directed to Lol pIa and Lol pIb, their derivatives, homologues or immunological relatives including derivatives containing the common antigenic epitope between Lol pIa and Lol pIb which are useful in developing a vaccine to desensitize humans to allergies due to grass pollen.

Accordingly, the present invention contemplates a method for desensitizing a human allergic to grass pollen which comprises administering to said human a desensitizing-effective amount of Lol pIa or Lol pIb, or at least one fragment of Lol pIa or Lol pIb, or a derivative, homologue, or immunological relative thereof or combinations thereof, whether made by recombinant or synthetic means, for a time and under conditions sufficient to effect desensitization of the human to the grass pollen.

The present invention, therefore, contemplates a pharmaceutical composition comprising a desensitizing or therapeutically effective amount of Lol pIa or Lol pIb, or at least one fragment of Lol pIa or Lol pIb or their derivatives, homologues or immunological relatives or combinations thereof and one or more pharmaceutically acceptable carriers and/or diluents. The active ingredients of a pharmaceutical composition comprising Lol pIa and/or Lol pIb and/or the like are contemplated to exhibit excellent therapeutic activity, for example, in the desensitization of humans allergic to grass pollen when administered in amount which depends on the particular case. For example, from about 0.5 ug to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intranasal, intradermal or suppository routes or implanting (e.g., using slow release molecules). Depending on the route of administration, the active ingredients which comprise Lol pIa and/or Lol pIb and/or the like may be required to be coated in a material to protect said ingredients from the action of enzymes, acids and other natural conditions which may inactivate said ingredients. For example, the low lipophilicity of Lol pIa and/or Lol pIb and/or the like will allow it to be destroyed in the gastrointestinal tract by enzymes capable of cleaving peptide bonds and in the stomach by acid hydrolysis. In order to administer LoI pIa and/or Lol pIb and/or the like by other than parenteral administration, they will be coated by, or administered with, a material to prevent their inactivation. For example, Lol pIa or the like may be administered in an adjuvant, co-administered with enzyme inhibitors or in liposomes. Adjuvant is used in its broadest sense and includes any immune stimulating compound, such as interferon. Adjuvants contemplated herein include resorcinols, non-ionic surfactants such as polyoxyethylene oleyl ether and n-hexadecyl polyethylene ether. Enzyme inhibitors include pancreatic trypsin. Liposomes include water-in-oil-in-water CGF emulsions as well as conventional liposomes.

The active compounds may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders of the extemporaneous dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The preventions of the action of microorganisms can be brought about by various antibacterial and antifungal agents, for example, parabens, chlorobutanol, phenol, sorbic acid, thimerosol, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When Lol pIa and/or Lol pIb or at least one fragment of Lol pIa and/or Lol pIb or the like are suitably protected as described above, the active compound may be orally administered, for example, with an inert diluent of with an assimilable edible carrier, or it may be enclosed in hard or soft shell gelatin capsule, or it may be compressed into tablets, or it may be incorporated directly with food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be carried and may conveniently be between about 5 to 80% of the weight of the unit. The amount of active compound in such therapeutically useful compositions is such that a suitable dosage will be obtained. preferred compositions or preparations according to the present invention are prepared so that an oral dosage unit form contains between about 10 ug and 2000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (1) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from 0.5 mg to about 2000 mg. Expressed in proportions, the active compound is generally present in from about 0.5 mg to about 2000 mg/ml of carrier. In the case of compositions containing supplementary active ingredients, the dosages are determined by reference to the usual dose and manner of administration of the said ingredients.

The present invention is further illustrated by the following non-limiting Figures and Examples.

EXAMPLES

Example 1

Isolation of cDNA Clones

A cDNA expression library in the vector lambda-gt 11 was prepared from polyadenylated mRNA of mature rye-grass pollen (Beall & Mitchell (1986) J. Immunol. Methods 86:217–223). This library was screened initially with monoclonal antibody (MAb) 40.1 (FIG. 1a).

Poly (A+) mRNA isolated from mature rye grass pollen by the phenol method (Herrin and Michaels (1984) Plant Mol. Biol. Reporter 2:24–29) was used to construct a cDNA library in the vector lambda-gt 11. The library was then screened with antibody probes to detect sequences expressing Group I proteins. E. coli Y1090 transfected with 3×10[4] recombinant phages were plated and incubated at 42° C. for 3 h. The plates were overlaid with a dry 132 mm nitrocellulose (NC) filters presoaked in 10 mM IPTG and transferred to 37° C. After incubation for 3 h the filters were carefully peeled off and incubated in 20 ml per filter of MTBS (10% w/v non-fat milk powder, 50 mm Tris-HCI, pH 7.6, 150 mM NaCl) for 30 min. at room temperature. A second set of NC filters was placed on phage plates and after incubating for 3 h were treated as above. Both sets of NC filters were tested for binding of MAb 40.1 to plaques by the method described in Huynh et al. (1985) in: DNA Cloning, A practical approach, Glover, D. M. (ed.) Vol. 1, pp. 49–78, IRL Press, Oxford, England. The antibody positive plaques were picked, purified, then replated and tested for binding to probes. The positive clones were plaque-purified and tested for IgE binding using sera from grass pollen-allergic subjects. Eighteen clones were selected as encoding proteins recognized by both Lol pI-specific MAbs and IgE antibodies (Table 1). The largest of the cDNA clones, 1.2 kb in size, that expressed rye-grass allergenic protein was initially selected for further characterization and sequencing, and designated clone lambda-12R (FIG. 1a).

TABLE 1

Characteristics of cDNA Clones Expressing Group I Allergens of Rye-grass

| Clone No. (___R) | Binding of MAb 12.3[a] | Binding of MAb 40.1[a] | Binding of IgE from sera of allergic idivs. | Approx. Size of Insert (bp) |
|---|---|---|---|---|
| 1 | – | – | – | |
| 2 | + | ++ | – | 700 |
| 3 | + | ++ | – | 600 |
| 4 | + | ++ | – | 800 |
| 5 | + | ++ | – | 500 |
| 6 | + | ++ | – | 600 |
| 7 | + | ++ | – | 400 |
| 8 | – | – | – | |
| 9 | – | – | – | |
| 10 | – | – | – | |
| 11 | + | ++ | – | 500 |
| 12 (Lol pIb) | ++ | + | ++ | 1200 |
| 13 (Lol pIa) | + | ++ | + | 800 |
| 14 | ++ | + | + | 1200 |
| 15 | – | – | – | |
| 16 | + | ++ | – | 800 |
| 17 | + | ++ | – | 400 |
| 18 | ++ | + | + | 1200 |

++ : -strongest binding
– : -no binding
MAb 12.3 shows high affinity for Lol pIb (clone 12R).
MAb 40.1 shows high affinity for Lol pIb (clone 13R).

Mab 12.3 shows high affinity for Lol pIb (clone 12R). Mab 40.1 shows high affinity for Lol pIa (clone 13R).

Figure 1B:
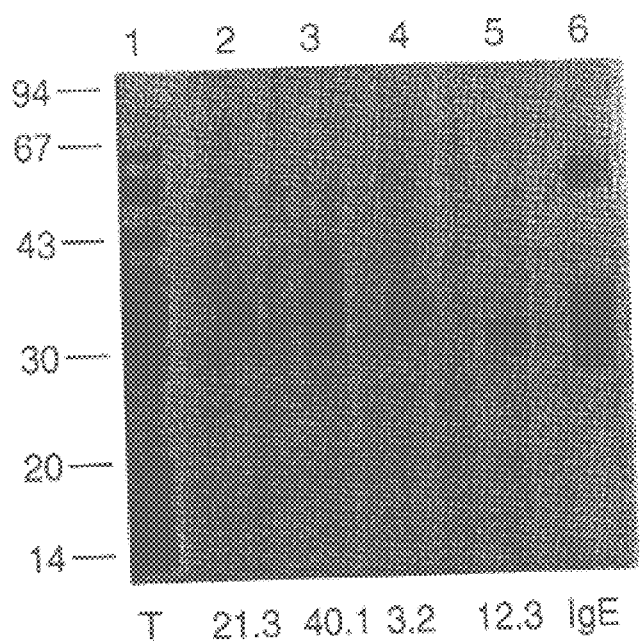

The specificity of IgE and MAbs was tested by immunoblot analysis of rye-grass pollen protein extracts (FIG. 1b).

Soluble proteins were extracted from rye-grass pollen by vigorous shaking in PBS (150 mM, pH 7.2) on ice for 3 h. Pollen was spun out of solution and the extracted protein standardized using the Biorad assay. 120 ug protein per lane was electrophoresed under reducing conditions on a 10–15% w/v SDS-polyacrylamide gel. Proteins were electroblotted onto NC filters and the blot blocked with TBS (10 mM Tris, 150 mM NaCl, pH 7.9) containing 10% w/v non-fat milk powder. The blot was cut into strips and each treated with the various probes: MAbs were diluted 1:1000 in TBS containing 1% BSA. Sera collected from at least 4 patients with high RAST scores for grass pollen, was pooled and used diluted 1:5 in TBS/1% w/v BSA for IgE binding. Horseradish peroxidase-conjugated secondary antibodies were used (Dakopatts) and after washing, binding was visualized with 4-chloro 1-naphthol (Biorad) and $H_2O_2$.

When the immunoblot was incubated in pooled sera from grass pollen-allergic individuals, strong IgE binding was observed throughout the 28–35 kD region. The MAbs used in this study, 3.2, 12.3, 21.3 and 40.1 had previously been partially characterized (Kahn and Marsh (1986) Molec. Immunol. 23:1281–1288; Singh and Knox (1985) Intl. Arch. Allergy and Applied. Immunol. 78:300–304; Smart et al. (1983) Intl. Arch. Allergy and Applied Immunol. 72:243–248). MAbs 3.2, 21.3 and 40.1 showed strong reactivity with the proteins in the 28–35 kD region. MAb 12.3 exhibited no binding to the 35 Kd band, but bound strongly to the lower bands. These interactions suggest that both IgE and MAbs can recognize denatured allergens, which makes them suitable probes for the detection of recombinant protein express in E. coli.

The allergen-beta-galactosidase fusion protein produced by the induction of lysogenic cultures of lambda-12R, was characterized by immunoblot analysis using MAb 40.1. This fusion protein of approximately 146 kD is assumed to be comprised of the 116 kD beta-galactosidase and 30 kD of allergen-encoded sequence. This fusion protein was produced in low yields. So in order to increase yields of the cloned allergen for further analysis, we used an alternative expression system. The 1.2 kb insert was subcloned in the pGEXl-3 series of plasmid expression vectors. These plasmids give a fusion polypeptide with the carboxyl terminus of the *Schistosoma japonicum* glutathione S-transferase protein (Smith and Johnson (1988) Gene 67:31–40). Strong IgE binding was detected only in bacteria transformed with pGEX-12R, and not in those with parental pGEX plasmids (data not shown, but similar binding shown in FIG. 4). Probing of Western blots with control sera that had negative radioallergosorbent (RAST) score for rye-grass pollen showed no IgE binding.

Example 2

Identity of Cloned Allergen 12R and 13R

All four MAbs used in this study recognized the cloned allergen 12R (FIG. 1*a*).

Not all MAbs show the same specificity to the native Lol pI proteins (FIG. 1*b*). In particular, MAb 12.3 does not recognize the 35 kD band. Because the cloned allergen binds all the MAbs, and with high intensity to MAb 12.3, it is predicted that the cloned allergen is likely to correspond to a protein of lower Mr, and not to the 35 kD protein. To confirm its identity, an immunological approach developed for parasite antigens was employed (eg Beall & Mitchell (1986) J. Immunol. Methods 86:217–223). In this method, the cloned allergen 12R was immobilized on nitrocellulose membrane, and used to bind specific IgE antibodies from sera. Bound antibodies were eluted and used to probe a Western blot of rye-grass pollen proteins. Highly specific and reproducible patterns of binding were consistently obtained in several experiments to two protein components of molecular weight 31 and 33 kD. No specific binding was observed when IgE antibodies from non-grass pollen allergic individuals were used now when extracts of *E. coli* transformed with non-recombinant pGEX plasmids were used to select IgE antibodies.

These experiments demonstrate that IgE antibodies that bind to clone 12R recognize two components with slightly different molecular weights, 31 and 33 kD. The 31/33 and 35 kD components may be structurally different in terms of their physico-chemical characteristics, and are tentatively designated Lol pIa (clone 13, 35 kD component) and Lol pIb (31/3.3 kd components).

To test this hypothesis, Lol pIa and Lol pIb proteins were purified by two-dimensional analysis involving preparative iso-electric focusing in the first dimension, followed by SDS-PAGE of the individual fractions collected. This procedure successfully separated Lol pIa (pI 5.5) and Lol pIb (pI 9.0) in sufficient quantity for their N-terminal sequence to be determined (Table 2).

TABLE 2

N-Terminal Amino Acid Sequences
Of Grass Pollen Allergens Obtained
In This Study Compared With Reported Sequences

| Allergen | N-terminal sequence |
|---|---|
| Lol pI | IAKV?PG??I TAEYGDKWLD AKSTWYGKPY |
| Lol pIa | IAKVPP*GP*WI TAEYGDKWLD AK T------ |
| Clone 13R | IAKVPPGPNI TAEYGDKWLD AKSTWYGKPT |
| Lol pIb | ADAGYTPAA? ?TPATPA?T |
| Clone 12R | ADAGYTPAAA ATPATPAATPA GGWRE |
| Lol pII | AAPVEFTVEK GSDEKNLALS IKYNKEGDSMA |
| Lol pIII | -TKVDLTVEK GSDAKTLVLN IKYTRPGDTLA |

*Indicates Hydroxyproline residue. The N-terminal sequences in Table 2 have the following Sequence Listing numbers: Lol pI-SEQ ID NO: 19; Lol pIa-SEQ ID NO: 20; Clone 13R-SEQ ID NO: 21; Lol pIb-SEQ ID NO: 22; Clone 12R - SEQ ID NO: 23; Lol pII-SEQ ID NO: 24, Lol pIII-SEQ ID NO: 25.

Individual protein components were isolated using preparative isoelectric focussing on the Rotofor (Biorad). The proteins were separated on SDS-PAGE, and transferred to PVDF membrane (Millipore). N-terminal sequencing was performed according to Matsudaira (1987) J. Biol. Chem. 262:10035–10038, and Simpson et al. (1989) J. Chromatogr. 476:345–361.

Figure 3A:
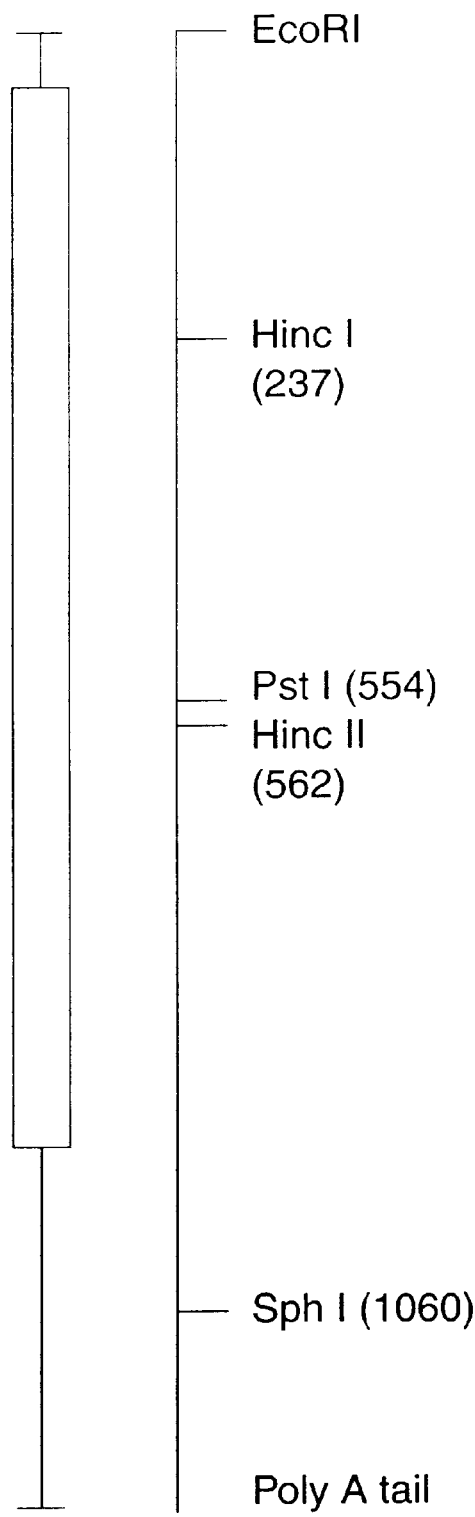

The sequence of the 35 kD allergen shows homology with the previously published sequence of Lol pI (Table 2). The 31/33 kD protein, Lol pIb, has a different N-terminal amino acid sequence from Lol pIa. It is concluded that the allergen encoded by clone 12R represents a major newly identified allergen, Lol pIb and that clone 13R encodes allergen Lol pIa. The nucleotide sequences of clones 12R (SEQ ID NO: 1) and 13R (SEQ ID NO: 3) are shown in FIGS. 3 and 6, respectively. The predicted amino acid sequences are also shown in SEQ ID NO: 2 (clone 12R) and SEQ ID NO: 4 (clone 13R).

Clones 4R, 6R, 16R and 17R (Table 1) were also sequenced and found to be partial clones of Lol pIa (SEQ ID NO: 5). The relative position of the sequenced clones with respect to the full-length nucleotide sequence of Lol pIa (SEQ ID NO: 5) is shown in Table 3.

TABLE 3

Summary of antibody binding to Lol pI cDNA clones

| Clone | FMC-A1 | FMC-A7 | IgE | Nucleotide Position in Lol pIa sequence |
|---|---|---|---|---|
| 4R  | ++ | + | − | 0–764   |
| 6R  | ++ | + | − | 159–754 |
| 16R | ++ | + | − | 12–764  |
| 17R | ++ | + | − | 383–756 |

Example 3

Pollen-specific Expression of Allergens

Poly A+ RNAs were isolated from different plant tissues: seed, leaf, root and pollen. 20 ug of total RNA from the different tissues was electrophoresed on a 1.2% w/v agarose gel in the presence of formamide and formaldehyde (Sambrook et al., supra), transferred to Hybond-C extra (Amersham, Arlington Heights, Ill.) and the filters baked at 80° C. for 2 h. The 1.2 kb 12R cDNA was radio-labelled with $^{32}p$ and incubated with the NC filter at 65° C. in the presence of 50% v/v formamide. The membrane was washed with 2xSSC containing 0.1% W/v SDS at 65° C.

Proteins were isolated from the different tissues (flower, leaf, root and pollen) by grinding in 10 mM PBS containing 1 mM PMSF, and immunoblotted (10 ug protein per lane) with the indicated antibodies. The binding was visualized by using $^{125}I$-goat anti-mouse Ig (Amersham) for MAbs, and polyclonal $^{125}I$-goat anti-human IgE (Kallestad, USA followed by autoradiography.

Figure 2A:
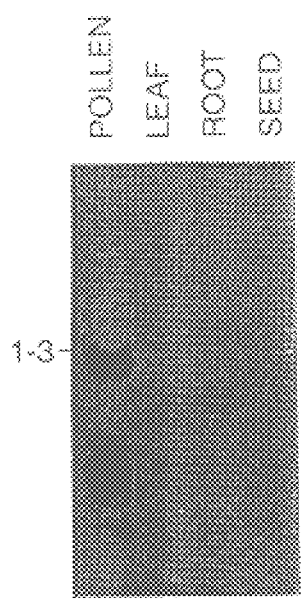
FIG. 2 shows tissue-type and cell-type specific expression of group I allergen transcripts.
Figure 2B:
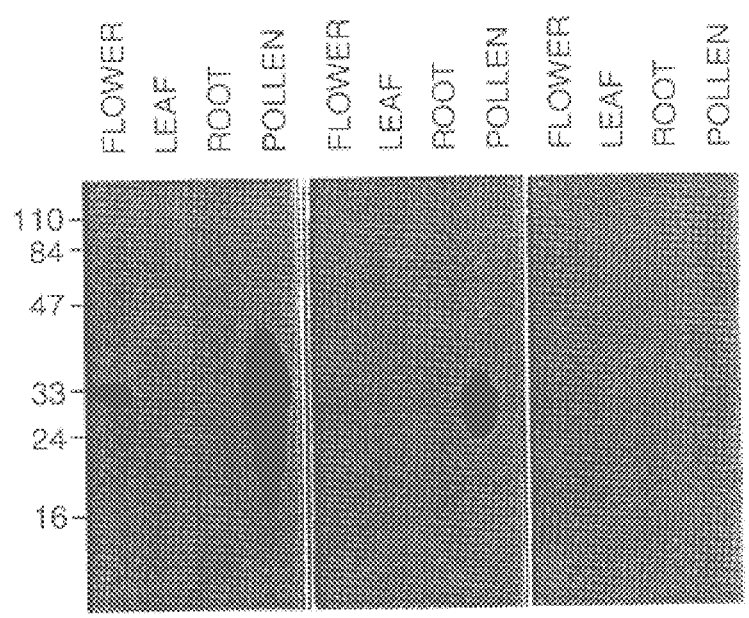

Northern blot analysis of RNA prepared from pollen showed high levels of expression of the cloned allergen gene in pollen but not in any vegetative tissues. A prominent band approximately 1.3 kb long is not detectable in RNA from vegetative tissues (FIG. 2a). Pollen-specific RNA expression corresponded to pollen-specific expression of antigens recognized by MAbs 40.1, 12.3 and IgE antibodies (FIG. 2b). Specific binding occurred only when pollen and floral tissues (containing pollen) were used as protein source.

Example 4

Primary Structure Analysis

The cDNA clone 12R was isolated, and subcloned into pGEM-3Z vectors (Promega, Madison, Wis.), restriction mapped, and resubcloned in various sized restriction fragments into pGEM vectors. DNA sequence was determined by double-stranded sequencing carried out by the dideoxy chain termination method (Sanger et al. (1977) Proc. Natl Acad. Sci. USA 74:5463–5468), using Sequenase (U.S. Biochemical) and T7 DNA polymerase (Pharmacia, Piscataway, N.J.). Sequencing was carried out concurrently with both ddNTPs and 7-deaza dGTP. The reading frame was confirmed by sequencing two expression subclones in pGEX vector as detailed in FIG. 4. DNA sequence data were analyzed using the MELBDBSYS system (NBRF Protein Identification Resource, Washington, USA; GENBANK, Los Alamos National Laboratory, USA; EMBL, Heidelberg, Germany; Swissprot and the NBRF PIR protein databases).

The nucleotide sequence of the cDNA clone 12R (SEQ ID NO: 1) is GC-rich (68% GC, FIG. 3b). There is an open reading frame of 921 bp starting with an ATG initiation codon at position 40 and terminating with a TGA codon at position 964. The proposed translation initiation site and its flanking sequences share 89% homology with the consensus plant sequence AACAATGGC (positions 36–44), and can be considered as in optimum context with the presence of a purine at position −3 from the methionine codon. The open reading frame potentially encodes a protein of Mr 34.1 kD.

The predicted protein sequence, which is rich in alanine (23%) and proline (13%), has a putative signal or target peptide sequence of 25 amino acids (FIG. 3b) (SEQ ID NO: 2). This is indicative of a cleaved protein of Mr 31.3 kD. The N-terminal protein sequence of Lol pIb is identical to the deduced amino acid sequence of clone 12R immediately after the putative cleavage site of the signal peptide sequence. This confirms that the cDNA-12R encodes the Lol pIb allergenic protein and that the protein has a signal peptide sequence which is cleaved.

Figure 3C:
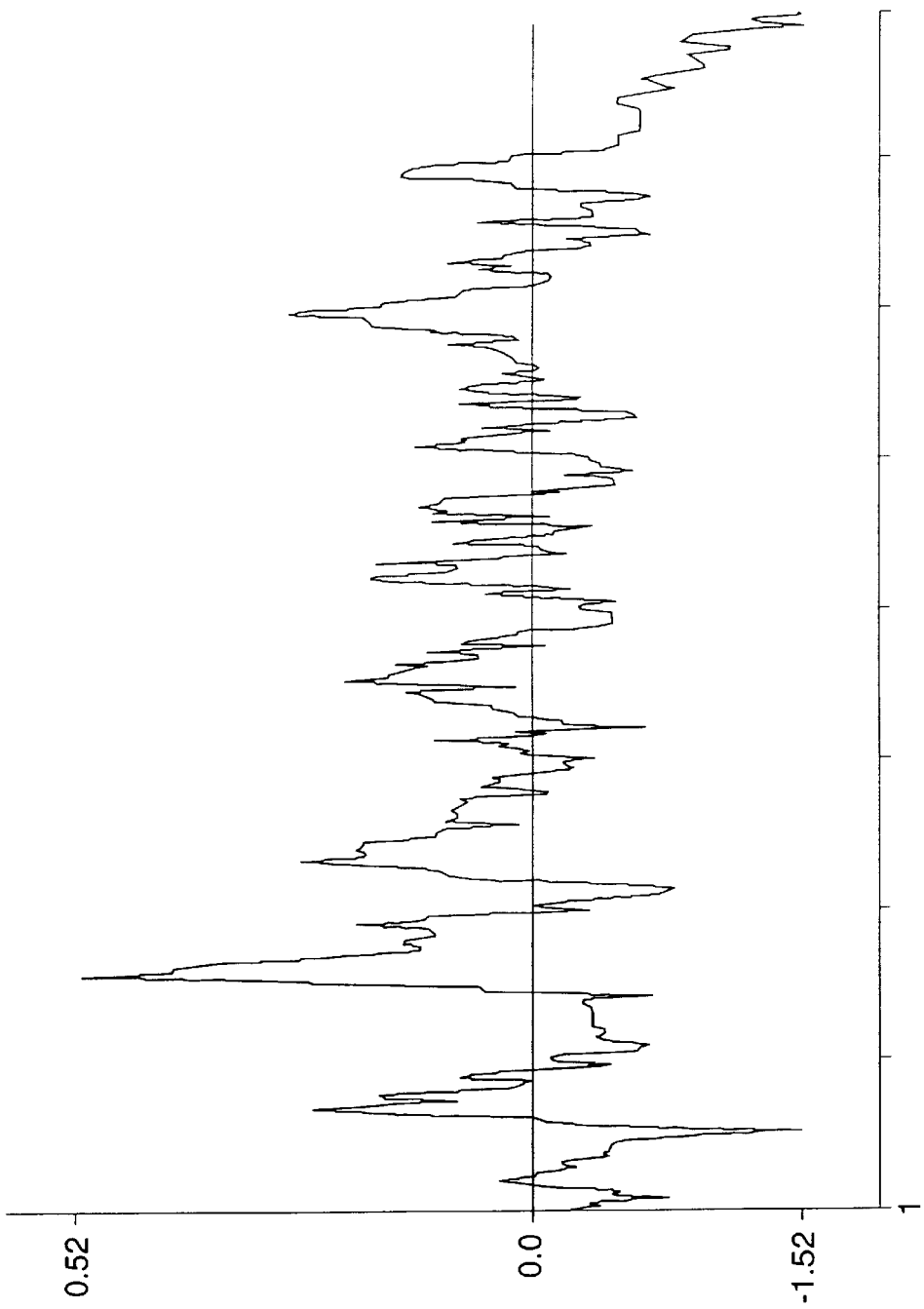

The signal sequence has features that are typical of other eukaryotic sequences: a relatively hydrophilic sequence of 5 amino acids at the C-terminus, a relatively hydrophobic sequence extending over most of the signal region which becomes more hydrophilic at the N-terminus (FIG. 3c). The amino acids at the C-terminus include alanine at the cleavage site, an aromatic residue tyrosine at −2, and a helix breaker proline at −6, all of which are common features of the C-terminal region of signal sequence.

A search of existing data-bases indicates no homology between the deduced amino acid sequence of lambda-12R and any other known protein. Furthermore, a search for consensus glycosylation sequences (Asn-x-Ser/Thr) in the deduced amino acid sequence detected no such sequences. The absence of an N-linked carbohydrate chain on the allergen was confirmed by the lack of deglycosylation following treatment with the enzymes N-glycanase and endo-F glycosidase. Chemical deglycosylation followed by SDS-PAGE showed no decrease in molecular weight of the protein. The 31/33 kD components remained as a doublet, suggesting that the difference in molecular weight is not due to glycosylation. The deglycosylation treatments did not affect IgE binding to the 31/33 kD components. As compared to Lol pIa which has 5% carbohydrate, no carbohydrate is present in Lol pIb.

Example 5

Delineation of IgE- and Mab-reacting Epitopes

To localize MAb and IgE determinants, an *E. coli* recombinant expression system was employed (Smith and Johnson (1988) Gene 67:31–40). Using this system, a number of restriction fragments were subcloned into the expression plasmid PGEX 1–3. The "in frame" sub-cloning of full length cDNA into pGEX, expressed the 61 kD fusion protein recognized by both IgE and MABs 40.1 and 12.3.

The full length cDNA 12R (SEQ ID NO: 1) or two restriction fragments 1H and 2P, were subcloned into plasmid expression vector pGEX. The procedure for inducing fusion proteins and preparation of bacterial lysates have been described earlier (Smith and Johnson, supra). The lysates obtained were subjected to reducing SDS-PAGE, followed by transfer to NC membranes. The blots were probed with IgE antibodies; and MAbs 40.1, 12.3 as described in FIG. 1b, except that $^{125}$I-anti-human IgE (Kallestad) was used to detect IgE binding.

Figure 4:
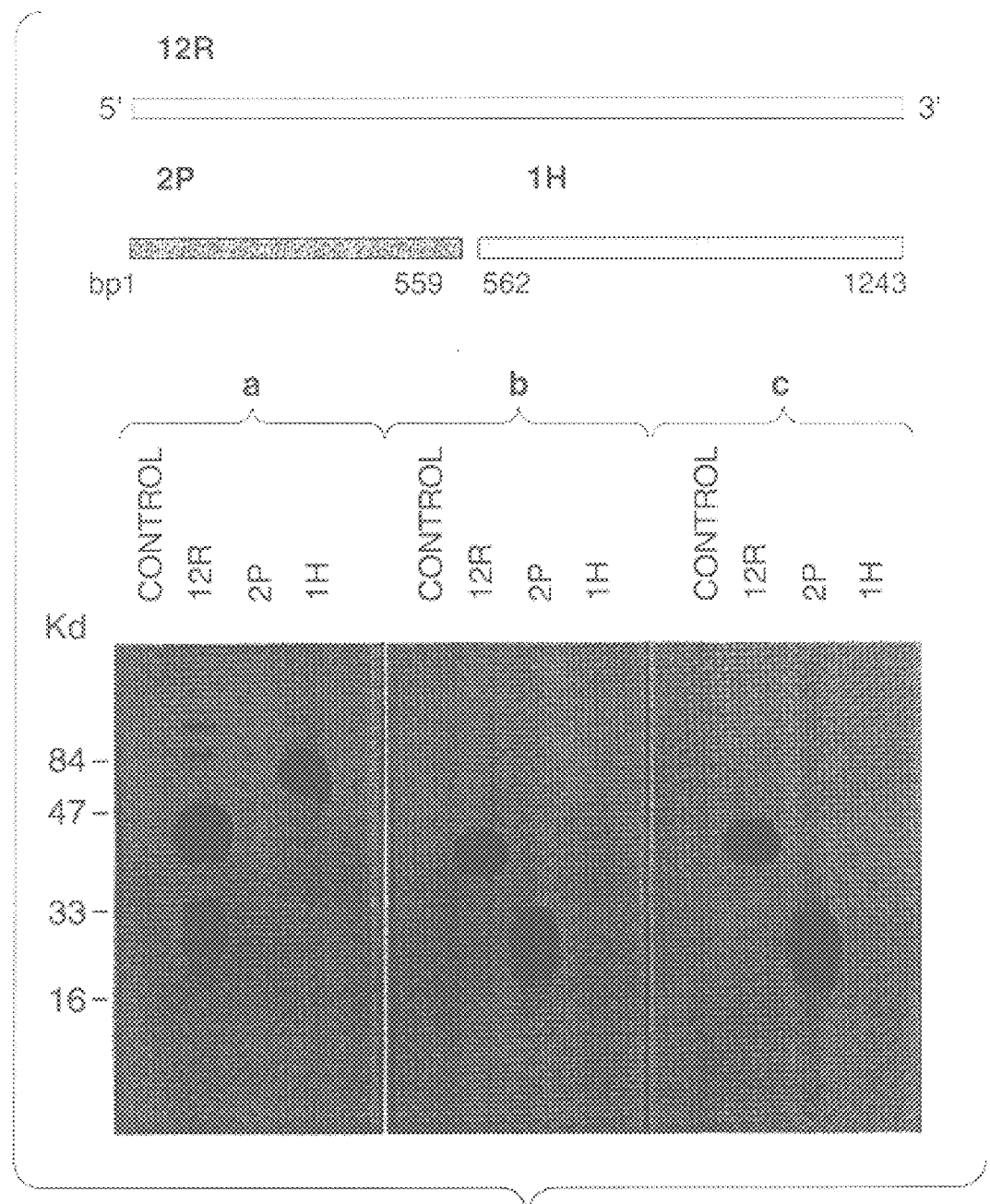
FIGS. 4a, 4b and 4c show the delineation of IgE and MAb-reacting epitopes in Lol pIb clone 12R using immunoblotting.

Immunoblot analysis showed that most of the fusion protein produced is cleaved by bacterial proteases near its fusion site with glutathione-S transferase, generating breakdown products which are recognized by IgE antibodies (FIG. 4). The recombinant fusion protein expressed by fragment 2P, although strongly reactive with both MAbs, was not recognized by IgE antibodies in pooled allergic sera. However, the N-terminally truncated protein produced by fragment 1H was not recognized by either of the MAbs, but was highly reactive with the IgE antibodies.

In this way, two distinct domains of the allergen molecule have been delineated: the N-terminal containing fragment has recognition sites for MAbs 12.3 and 40.1; and the C-terminal containing fragment 1H which shows strong IgE binding and thus has the allergenic determinant(s). Because the two MAbs have different binding specificities (FIG. 1b), the recognition sites for the two MAbs are likely to be different, although in the same fragment. Fine mapping with smaller fragments is needed to delineate the 12.3 and 40.1 binding sites, but these results are sufficient to show that the IgE determinant is different.

Example 6

Intracellular Targeting of Lol pIb in Rye-grass Pollen

Mature pollen of *Lolium perenne* was prepared for scanning electron microscopy according to established methods (Staff et al. (1990) Histochem J. 22:276–290). For immunocytochemistry, mature anthers were fixed under anhydrous conditions: 0.1% glutaraldehyde, 1% paraformaldehyde in 2,2-dimethoxypropane at 4° C. for 2 h and processed for transmission electron microscopy. (Staff et al., supra). This method has been developed to reduce diffusion of the allergens from their cellular sites in aqueous media. Blocks were polymerized in LR gold resin with 1% benzil at −25° C. under UV illumination and 80 nm thin sections picked up on gold grids. Immuno-labelling was first with primary antibody, MAb 12.3 (specific for Lol pIb) followed by gold-goat-anti-mouse IgG probe (15 nm particle size). This label was silver-enhanced to 40 nm particle size (modified from Danscher & Norgaard (1983) J. Histochem. Cytochem. 31:1394–1398. A second labelling was performed on the same sections with a mixture of three MAbs, 3.2, 21.3 and 40.1 (specific for Lol pIa) followed by gold-goat-anti-mouse IgG probe with 15nm particle size. Antibody specificity and method controls run as described previously (Staff et al., supra) showed no gold particles at these sites.

Figure 5A:
FIGS. 5a, 5b and 5c show detection of Lol pIa and Lol pIb in mature pollen of rye-grass using specific MAbs and immunogold probes.

Lol pI is located in the cytosol and not in the organelles (Staff et al., supra). These findings were obtained using immuno-gold probes with MAbs specific for Lol pI. As shown herein, MAb 12.3, which is specific for Lol pIb, binds predominantly to the starch grains (FIG. 5a, b). Grass pollen is filled with starch grains which are 1×2.5 um in size, and originate in the lumen of amyloplasts.

Figure 5B:
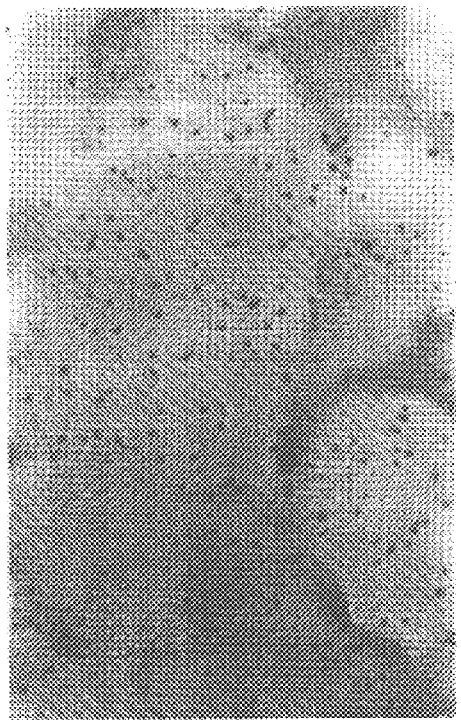
Figure 5C:

As shown in FIG. 5b, the large gold particles located predominantly over the starch grains (large electron-lucent spaces) show binding of MAb 12.3 to Lol pIb, while smaller particles over the cytosol are typical of binding to Lol pIa. Scale bar is 1 um. FIG. 5c shows the appearance of fresh, viable pollen after exposure to water for 30s, dark field illumination. Most pollen grains burst, extruding their cytoplasmic contents, including starch grains (white particles) through the germinal pore. Scale bar, 30 um.

The localization of Lol pIb in the plastids implies that this protein should be transported from the cytosol to the lumen of the plastids during development. For transport to chloroplasts, the proteins which are synthesized in the cytosol are synthesized as large precursors containing a target peptide sequence that is cleaved after transport intd the organelle. Comparison of the signal sequence of Lol pIb (FIG. 3b) (SEQ ID NO: 2, amino acids −25 through −1) with the domain structure of published mitochondrial and chloroplast-specific transit peptides is as below.

For import into plastids, plant signal peptides need additional information at the carboxyl terminus, which resides in −2 to −7 region from the cleavage site of the peptide (SEQ ID NO: 2). The signal peptide of most chloroplast-targeted proteins possesses the sequence "G-R-V" or functionally homologous sequence reading from the −2 position. The signal peptide of Lol pIb (clone 12R) has the sequence "G-R-S" in this position (FIG. 3b). Thus it is concluded that the Lol pIb molecule is synthesized first as a pre-allergen in the cytosol, and is transported to the plastid for post-translational modification. These intracellular processing steps may explain the appearance of the doublet 31/33 kD found by immunoblotting. The unprocessed pre-allergen is 33 kD, and after processing in the plastids, the mature protein is 31 kD. Both these forms co-exist in mature pollen. This doublet may also represent different lsoforms of Lol pIb.

Example 7

Presentation of Lol pIa and b to the Immune System

When the rye-grass flower opens, the anthers are exerted and the pollen is released into the air through a pore which opens at the base of each anther. Rye-grass shows the greatest pollen production of any grass, releasing approximately 460 kg of pollen per hectare into the atmosphere in pastures that are not mowed or grazed. Ninety-nine per cent of this pollen is deposited (and re-deposited) within 1 km of its source. Grass pollen is short-lived, yet it can remain for several days in the atmosphere. Experiments show that the pollen remains viable for only a few hours after release.

When viable, the grains can germinate on the stigma, or in artificial media with high levels of osmoticum. Living viable rye-grass pollen grains when exposed to water, burst at the single germinal aperture releasing the cytoplasmic contents (FIG. 5c). Prominent among the released contents are the starch grains. Media with high osmoticum, e.g. 30% w/v sucrose are required to maintain tonicity of the grains. In contrast, it is well-known that dead pollen grains which have no permeability barriers, act like a sponge. Cellular proteins, including allergens, are released from the surface upon moistening.

It is easy to see how grass pollen can trigger hay fever after contacting the oral and eye mucosa, by direct release of the allergens. The pollen grains themselves remain on the surface of the mucosa, but the released allergenic proteins pass through the mucosa and subepithelial layers where they interact with basophils and mast cells. It is less easy to see how pollen grains as large as 30–50 um in diameter can induce allergic asthma, a disease triggered by the presence of allergens in the airways of the lungs.

Recent evidence suggests that grass pollen allergens are associated with smaller micronic particles found in the atmospheric aerosol. The original of such particles is obscure. From the present results on allergen localization, and observations on pollen behavior in water, a new hypothesis is proposed to explain how grass pollen can induce allergic asthma in the lungs of susceptible humans. Starch grains are released as micronic particles into the atmospheric aerosol when the living pollen grains encounter water vapor, or water on the surface of a leaf or other substrata. These particles, both coated and filled with allergens, act as vehicles for allergen presentation to the upper and lower respiratory tract. Micronic particles can also, of course, results from the leaching of allergens from grass pollen and deposition on other components of the atmospheric aerosol.

Example 8

Isolation and Cloning of Nucleic Acid Sequence Coding for Lol pIa

Total mRNA was extracted from mature ryegrass pollen by the phenol method of Herrin and Michaels, supra. Double-stranded cDNA was synthesized from 1 μg of total mRNA using a commercially available kit (cDNA synthesis system plus kit, BRL, Gaithersburg, Md.). After a phenol extraction and ethanol precipitation, the cDNA was blunted with T4 DNA polymerase (Promega, Madison, Wis.), and ligated to ethanol-precipitated, self-annealed AT (SEQ ID No.: 7) and AL (SEQ ID NO: 8) oligonucleotides for use in a modified Anchored PCR reaction, according to the method in Rafnar et al. (1991) J. Biol. Chem. 266:1229–1236; Frohman et al. (1990) Proc. Hatl. Acad. Sci. USA 85; 8998–9002; and Roux et al. (1990) BioTech. 8:48–57. Oligonucleotide AT has the sequence 5'-GGGTCTAGAGGTACCGTCCGATCGATCATT-3' (SEQ ID NO: 7) (Rafnar et al. supra). Oligonucleotide AL has the sequence AATGATCGATGCT (SEQ ID NO: 8) (Rafnar et al. supra.).

Polymerase chain reactions (PCR) were carried out using a commercially available kit (GeneAmp® DNA Amplification kit, Perkin Elmer Cetus, Norwalk, Conn.) whereby 10 μl 10x buffer containing dNTPs was mixed with 1 μg each of primer AP, which has the sequence 5'-GGGTCTAGAGGTACCGTCCG-3' (SEQ ID NO: 9) (Rafner et al. supra.) and LpA-5, which has the sequence 5'-CCCTGCAGATTATTTGAGATCTTGAG-3' (SEQ ID NO: 10), cDNA (3–5 μl of a 20 μl linkered cDNA reaction mix), 0.5 μl Amplitaq DNA polymerase, and distilled water to 100 μl.

Nucleotides 1 through 8 (5'-CCCTGCAG) of LpA-5 (SEQ ID NO: 10) correspond to a Pst I site added for cloning purposes; the remaining nucleotides correspond to the non-coding strand sequence complementary to nucleotides 483 through 500 of SEQ ID NO: 3.

The samples were amplified with a programmable thermal controller (MJ Research, Inc., Cambridge, Mass.). The first 5 rounds of amplification consisted of denaturation at 94° C. for 1 minute, annealing of primer to the template at 45° C. for 1.5 minutes, and chain elongation at 70° C. for 2 minutes. The final 20 rounds of amplification consisted of denaturation as above, annealing at 55° C. for 1.5 minutes, and elongation as above. Five percent (5 μl) of this initial amplification was then used in a secondary amplification whereby 10 μl 10x buffer containing dNTPs was mixed with 1 μg each of primer AP (SEQ ID NO: 9) and primer LpA-3, which has the sequence 5'-CCCTGCAGTCATGCTCACTTGGCCGAGTA-3' (SEQ ID NO: 11), 0.5 μl Amplitaq DNA polymerase, and distilled water to 100 μl. The secondary PCR reaction was performed as described herein. Nucleotides 1 through 8 (5'-CCCTGCAG-3') of LpA-3 (SEQ ID NO: 11) correspond to a Pst I site added for cloning purposes; nucleotides 9 through 12 (5'-TCA-3') correspond to the complementary sequence for a new stop codon, and the remaining nucleotides correspond to the non-coding strand sequence complementary to nucleotides 793 through 810 of SEQ ID NO: 5 (nucleotides 426 through 443 of SEQ ID NO: 3), including translated sequence of Lol pIa (SEQ ID NO: 5), the native stop codon and 3' untranslated sequence.

Amplified DNA was recovered by sequential chloroform, phenol, and chloroform extractions, followed by precipitation at −20° C. with 0.5 volumes of 7.5 ammonium acetate and 1.5 volumes of isopropanol. After precipitation and washing with 70% ethanol, the DNA was simultaneously digested with Xba I and Pst I in a 15 μl reaction and electrophoresed through a preparative 3% GTG NuSieve low melt gel (FMC, Rockport, Me.). The appropriate sized DNA band was visualized by EtBr staining, excised, and ligated into appropriately digested M13mp18. for sequencing by the dideoxy chain termination method (Sanger et al. (1977) Proc. Natl Acad Sci USA 74:5463–5476) using a commercially available sequencing kit (Sequenase kit, U.S. Biochemicals, Cleveland; Ohio).

Both strands were sequenced using M13 forward and reverse primers (N.E. BioLabs, Beverly, Mass.) and internal sequencing primers LpA-13 (SEQ ID NO: 12), LpA-12 (SEQ ID NO: 13), LpA-9 (SEQ ID NO: 14), LpA-2 (SEQ ID NO: 15), LpA-7 (SEQ ID NO: 16), LpA-10 (SEQ ID NO: 17), and LpA-IA (SEQ ID NO.: 18). LpA-13 has the sequence 5'-GAGTACGGCGACAAGTGGC-3' (SEQ ID NO: 12), which corresponds to nucleotides 121 through 139 of SEQ ID NO: 5. LpA-12 has the sequence 5'-TTCGAGATCAAGTGCACC-3' (SEQ ID NO: 13), which corresponds to nucleotides 310 through 318 of SEQ ID NO: 5. LpA-9 has the sequence 5'-GTGACAGCCTCGCCGG-3' (SEQ ID NO: 14), which corresponds to the non-coding strand sequence complementary to nucleotides 335 through 350 of SEQ ID NO: 5. LpA-2 has the sequence 5'-GGGAATTCCATGGCGAAGAAGGGC-3' (SEQ ID NO: 15). Nucleotides 1 through 7 (5-GGGATT-3') of SEQ ID NO: 15 correspond to part of an Eco-RI restriction site added for cloning purposes; the remaining sequence of SEQ ID NO: 15 corresponds to nucleotides 425 through 441 of SEQ ID NO: 5. LpA-7 has the sequence 5'-GTGCCGTCCGGGTACT-3' (SEQ ID NO: 16), and corresponds to non-coding strand sequence complementary to nucleotides 503 through 518 of SEQ ID NO: 5. LpA-10 has the sequence 5'-CCGTCGACGTACTTCA-3' (SEQ ID NO: 17), which corresponds to non-coding strand sequence complementary to nucleotides 575 through 590 of SEQ ID NO: 5. LPA-IA has the sequence 5'-GGAGTCGTGGGGAGCAGTC-3' (SEQ ID NO: 18), which corresponds to nucleotides 654 through 672 of SEQ ID NO: 5.

Multiple clones from several independent PCR reactions werp sequenced. The sequence of a representative clone of Lol pIa, clone 26.j, with the deduced amino acid sequence is shown in FIGS. 7*a* and 7*b* (SEQ ID NO: 5). As shown in FIGS. 7*a* and 7*b*, the nucleic acid sequence coding for Lol pIa has an open reading frame beginning with an ATG initiation codon at nucleotide 16 (SEQ ID NO: 5, nucleotide base 16) and ending with a TGA stop codon at nucleotide 805 (SEQ ID NO: 5, nucleotide base 805). The translated protein has a deduced amino acid sequence of 263 amino acids with a predicted molecular weight and pI of 28.4 kD and 5.55 respectively. The initiating methionine is numbered amino acid −23, with amino acid numbered +1 corresponding to the NH2-terminus of the mature protein, as defined by amino acid sequencing (Cottam et al (1986) Biochem. J. 234:305–310). Amino acids −23 through −1 in FIG. 7 (SEQ ID NO: 5, amino acids −23 through −1) correspond to a leader sequence that is cleaved from the mature protein; the mature protein is therefore composed of 240 amino acids and has a predicted molecular weight and pI of 26.1 kD and 5.38 respectively. There is a single potential N-linked glycosylation site at amino acid 9.

Clone 26.j was deposited with the American Type Culture Collection, 12301 Parklawn Drive, Rockville, Md. 20853 on Oct. 2, 1997 as pUC plasmid with insert in *Escherichia coli* pUC 19/26j; Lol pI in JM 109 and assigned ATCC Deposit No. 98553.

Amino acids 1 through 30 of clone 26.j (SEQ ID NO: 5) correspond exactly to the published sequence of the $NH_2$ terminus of Lol pI (Cottam et al., supra). Amino acids 213 through 240 of clone 26.j (SEQ ID NO: 5) correspond exactly to the published internal amino acid sequence of Lol pI (Esch and Klapper (1989) Mol. Immunol. 26:557–561).

The first nucleotide of clone 13R (SEQ ID NO: 3) corresponds to nucleotide 368 of Lol pIa (SEQ ID NO: 5).

Example 9

Identification of Polymorphisms in Lol pIa

A number of polymorphisms in the nucleotide sequence coding for Lol pIa were discovered during the amplification and sequencing of different Lol pIa clones. Some of the polymorphisms cause an amino acid change relative to that of clone 26.j, while others are silent polymorphisms that do not cause an amino acid change. The polymorphisms found in the sequence coding for Lol pIa are summarized in Table 4. The nucleotide base numbers are those of the sequence of clone 26.j shown in FIGS. 7a and (SEQ ID NO: 5).

TABLE 4

POLYMORPHISMS DETECTED IN Lol pIa

|   | Nucleotide Polymorphism | Amino Acid Polymorphism |
|---|---|---|
| 1 | $GGC_{215} \rightarrow GGA/GGT$ | NONE |
| 2 | $G_{234}AC_{236} \rightarrow GAT$ | $D_{45} \rightarrow N$ |
| 3 | $GTT_{239} \rightarrow GTC$ | NONE |
| 4 | $CGT_{351} \rightarrow CGC$ | NONE |

TABLE 4-continued

POLYMORPHISMS DETECTED IN Lol pIa

|   | Nucleotide Polymorphism | Amino Acid Polymorphism |
|---|---|---|
| 5 | $GGC_{356} \rightarrow GGT$ | NONE |
| 6 | $AAC_{389} \rightarrow AAT$ | NONE |
| 7 | $CCC_{398} \rightarrow CCT$ | NONE |
| 8 | $CAT_{413} \rightarrow CAC$ | NONE |
| 9 | $GCC_{434} \rightarrow GCA$ | NONE |
| 10 | $GAC_{530} \rightarrow GAT$ | NONE |
| 11 | $GG_{532}C \rightarrow GAC$ | $G_{144} \rightarrow D$ |
| 12 | $CCG_{542} \rightarrow CCA$ | NONE |
| 13 | $ACA_{545} \rightarrow ACG$ | NONE |
| 14 | $GC_{562}T \rightarrow GGT$ | $A_{154} \rightarrow G$ |
| 15 | $CTC_{581} \rightarrow CTG$ | NONE |
| 16 | $GCG_{626} \rightarrow GCC$ | NONE |
| 17 | $ATC_{782} \rightarrow ATT$ | NONE |
| 18 | $CCT_{785} \rightarrow CCC$ | NONE |

All confirmed nucleotide polymorphisms (polymorphisms observed in the sequence analysis of clones from two independent PCR reactions) are shown relative to the sequence of clone 26.j (SEQ ID NO: 5). The polymorphic residues in their respective codon triplets are numbered. Productive amino acid changes are also shown; most nucleotide polymorphisms are silent and do not result in an amino acid change. Twenty-eight potential polymorphisms have only been observed in clones from single PCR reactions. Seventeen of these 28 potential polymorphisms are silent mutations and do not result in an amino acid polymorphism; the remaining 11 potential polymorphic sites would result in the following amino acid changes, specifically: $T_{11} \rightarrow M$, $A_{49} \rightarrow V$, $R_{67} \rightarrow S$, $K_{79} \rightarrow R$, $V_{90} \rightarrow I$, $Q_{133} \rightarrow R$, $I_{162} \rightarrow T$, $V_{173} \rightarrow E$, $I_{187} \rightarrow T$, $V_{223} \rightarrow F$ and $K_{232} \rightarrow R$.

Those skilled in the art will appreciate that the invention described is susceptible to variations and modification other than those specifically described. It is understood that the invention includes all such variations and modifications. The invention also includes all steps, features, compositions and compounds referred to or indicated in this specification, individually or collectively, and any and all combinations of any two or more of said steps or features.

The nucleotide sequences presented herein represent the most accurate data presently available. Minor corrections may subsequently be made to the sequences without departing from the scope of the present invention.

What is claimed is:

1. A method of treating sensitivity to ryegrass pollen in a mammal sensitive to such pollen, comprising administering to said mammal a therapeutically effective amount of an isolated ryegrass pollen allergen Lol p Ia encoded by the nucleotide sequence of SEQ ID NO: 3 or SEQ ID NO:5.

2. A method of treating sensitivity to ryegrass pollen in a mammal sensitive to such pollen, comprising administering to said mammal a therapeutically effective amount of an isolated ryegrass pollen allergen Lol p Ia comprising the amino acid sequence of SEQ ID NO: 4, SEQ ID NO:6, or the mature portions thereof.

3. A method of treating sensitivity to ryegrass pollen in a mammal sensitive to such pollen, comprising administering to said mammal a therapeutically effective amount of an antigenic fragment of a ryegrass pollen allergen Lol p Ia having the amino acid sequence of SEQ ID NO: 4 or SEQ ID NO:6, wherein said antigenic fragment comprises at least one epitope of said pollen allergen.

4. The method of claim 3, wherein the epitope is a T cell epitope.

5. The method of claim 3, wherein the epitope is a B cell epitope.

6. The method of claim 3, wherein the Lol p Ia pollen allergen or antigenic fragment thereof is produced by chemical synthesis or by recombinant expression.

7. A method of treating sensitivity to ryegrass pollen in a mammal sensitive to such pollen, comprising administering to said mammal a therapeutically effective amount of an isolated ryegrass pollen allergen or antigenic fragment thereof capable of stimulating T cells specific for a ryegrass Lol p Ia pollen allergen comprising the amino acid sequence of SEQ ID NO: 4 or SEQ ID NO:6.

8. A method of treating sensitivity to ryegrass pollen in a mammal sensitive to such pollen, comprising administering to said mammal a therapeutically effective amount of an an isolated Lol p Ia pollen allergen which is a polymorphic variant of a ryegrass Lol p Ia pollen allergen comprising the amino acid sequence of SEQ ID NO: 4 or SEQ ID NO:6.

9. A therapeutic composition comprising an isolated ryegrass pollen allergen Lol p Ia encoded by the nucleotide sequence of SEQ ID NO: 3 or SEQ ID NO:5 and a pharmaceutically acceptable carrier.

10. A therapeutic composition comprising an isolated ryegrass pollen allergen Lol p Ia comprising the amino acid sequence of SEQ ID NO: 4, SEQ ID NO:6, or the mature portions thereof, and a pharmaceutically acceptable carrier.

11. A therapeutic composition comprising an antigenic fragment of a ryegrass pollen allergen Lol p Ia having the amino acid sequence of SEQ ID NO: 4 or SEQ ID NO:6, wherein said antigenic fragment comprises at least one epitope of said pollen allergen, and a pharmaceutically acceptable carrier.

12. The therapeutic composition of claim 11, wherein the epitope is a T cell epitope.

13. The therapeutic composition of claim 11, wherein the epitope is a B cell epitope.

14. The therapeutic composition of claim 11, wherein the Lol p Ia pollen allergen or antigenic fragment thereof is produced by chemical synthesis or by recombinant expression.

15. A therapeutic composition comprising an isolated ryegrass pollen allergen or antigenic fragment thereof capable of stimulating T cells specific for a ryegrass Lol p Ia pollen allergen comprising the amino acid sequence of SEQ ID NO: 4 or SEQ ID NO:6, and a pharmaceutically acceptable carrier.

16. A therapeutic composition comprising an isolated Lol p Ia pollen allergen which is a polymorphic variant of a ryegrass Lol p Ia pollen allergen comprising the amino acid sequence of SEQ ID NO: 4 or SEQ ID NO:6, and a pharmaceutically acceptable carrier.

* * * * *

SEQUENCE LISTING

```
<160> NUMBER OF SEQ ID NOS: 25

<210> SEQ ID NO 1
<211> LENGTH: 1242
<212> TYPE: DNA
<213> ORGANISM: Lolium perenne
<220> FEATURE:
<221> NAME/KEY: mat_peptide
<222> LOCATION: (115)..(963)
<221> NAME/KEY: CDS
<222> LOCATION: (40)..(963)

<400> SEQUENCE: 1
cgctatccct ccctcgtaca aacaaacgca agagcagca atg gcc gtc cag aag      54
                                           Met Ala Val Gln Lys
```

-continued

```
                                   -25
tac acg gtg gct cta ttc ctc cgc cgt ggc cct cgt ggc ggg ccc ggc    102
Tyr Thr Val Ala Leu Phe Leu Arg Arg Gly Pro Arg Gly Gly Pro Gly
-20             -15             -10             -5 cgc tcc tac gcc gct gac gcc ggc tac acc ccc gca gcc gcg gcc acc    150
Arg Ser Tyr Ala Ala Asp Ala Gly Tyr Thr Pro Ala Ala Ala Ala Thr
            -1  1               5                   10 ccg gct act cct gct gcc acc ccg gct ggc ggc tgg agg gaa ggc gac    198
Pro Ala Thr Pro Ala Ala Thr Pro Ala Gly Gly Trp Arg Glu Gly Asp
        15              20              25 gac cga cga gca gaa gct gct gga gga cgt caa cgc ctg gct tca agg    246
Asp Arg Arg Ala Glu Ala Ala Gly Gly Arg Gln Arg Leu Ala Ser Arg
    30              35              40 cag ccg tgg ccg ccg ctg cca acg ccc ctc cgg cgg aca agt tca aga    294
Gln Pro Trp Pro Pro Leu Pro Thr Pro Leu Arg Arg Thr Ser Ser Arg
45              50              55              60 tct tcg agg ccg cct tct ccg agt cct cca agg gcc tcc tcg ccc acc    342
Ser Ser Arg Pro Pro Ser Pro Ser Pro Pro Arg Ala Ser Ser Pro Thr
                65              70              75 tcc gcc gcc aag gca ccc ggc ctc atc ccc aag ctc gac acc gcc tac    390
Ser Ala Ala Lys Ala Pro Gly Leu Ile Pro Lys Leu Asp Thr Ala Tyr
            80              85              90 gac gtc gcc tac aag gcc gcc gag gcc cac ccc cga ggc caa gta cga    438
Asp Val Ala Tyr Lys Ala Ala Glu Ala His Pro Arg Gly Gln Val Arg
        95              100             105 cgc ctt cgt cac tgc cct cac cga agc ctc cgc gtc atc gcc ggc gcc    486
Arg Leu Arg His Cys Pro His Arg Ser Leu Arg Val Ile Ala Gly Ala
    110             115             120 ctc gag gtc cac gcc gtc aag ccc gcc acc gag gag gtc ctc gct gct    534
Leu Glu Val His Ala Val Lys Pro Ala Thr Glu Glu Val Leu Ala Ala
125             130             135             140 aag atc ccc acc ggt gag ctg cag atc gtt gac aag atc gat gct gcc    582
Lys Ile Pro Thr Gly Glu Leu Gln Ile Val Asp Lys Ile Asp Ala Ala
                145             150             155 ttc aag atc gca gcc acc gcc gcc aac gcc gcc ccc acc aac gat aag    630
Phe Lys Ile Ala Ala Thr Ala Ala Asn Ala Ala Pro Thr Asn Asp Lys
            160             165             170 ttc acc gtc ttc gag agt gcc ttc aac aag gcc ctc aat gag tgc acg    678
Phe Thr Val Phe Glu Ser Ala Phe Asn Lys Ala Leu Asn Glu Cys Thr
        175             180             185 ggc ggc gct atg aga cct aca agt tca tcc cct ccc tcg agg ccg cgg    726
Gly Gly Ala Met Arg Pro Thr Ser Ser Ser Pro Pro Ser Arg Pro Arg
    190             195             200 tca agc agg cct acg ccg cca ccg tcg ccc gcc gcg ccc gag gtc aag    774
Ser Ser Arg Pro Thr Pro Pro Ser Pro Ala Ala Pro Glu Val Lys
205             210             215             220 tac gcc gtc ttt gag gcc gcg ctg acc aag gcc atc acc gcc atg acc    822
Tyr Ala Val Phe Glu Ala Ala Leu Thr Lys Ala Ile Thr Ala Met Thr
                225             230             235 cag gca cag aag gcc ggc aaa ccc gct gcc gcc gct gcc aca gcg gcc    870
Gln Ala Gln Lys Ala Gly Lys Pro Ala Ala Ala Ala Thr Ala Ala
            240             245             250 gca acc gtt gcc acc gcg gcc gca acc gcc gcc gcc gtg ctg cca ccg    918
Ala Thr Val Ala Thr Ala Ala Ala Thr Ala Ala Ala Val Leu Pro Pro
        255             260             265 ccg ctg ctg gtc gta caa agc ctg atc agc ttg cta ata tac tac       963
Pro Leu Leu Val Val Gln Ser Leu Ile Ser Leu Leu Ile Tyr Tyr
    270             275             280 tgaacgtatg taagtgcatg atccgggcgg cgagtggttt tgttgataat taatcttcgt   1023
```

-continued

```
tttcgttttc atgcagccgc gatcgagagg ttgcatgctt gtaataattc aatattttc    1083 atttcttttt gaatctgtaa atccccatga caagtagtgg gatcaagtcg gcatgtatca    1143
ccgttgatgc gagtttaacg atggggagtt tatcaaagaa tttattatta aaaaaaaaa    1203 aaaaaaaaaa aaaaaaaaaa aaaaaaaaaa aaaaaaaaa                           1242
```

<210> SEQ ID NO 2
<211> LENGTH: 308
<212> TYPE: PRT
<213> ORGANISM: Lolium perenne

<400> SEQUENCE: 2

```
Met Ala Val Gln Lys Tyr Thr Val Ala Leu Phe Leu Arg Arg Gly Pro
-25              -20              -15              -10

Arg Gly Gly Pro Gly Arg Ser Tyr Ala Ala Asp Ala Gly Tyr Thr Pro
             -5               -1  1                5

Ala Ala Ala Thr Pro Ala Thr Pro Ala Ala Thr Pro Ala Gly Gly
              10              15              20

Trp Arg Glu Gly Asp Asp Arg Arg Ala Glu Ala Ala Gly Gly Arg Gln
     25              30              35

Arg Leu Ala Ser Arg Gln Pro Trp Pro Pro Leu Pro Thr Pro Leu Arg
40              45              50              55

Arg Thr Ser Ser Arg Ser Ser Arg Pro Pro Ser Pro Ser Pro Pro Arg
             60              65              70

Ala Ser Ser Pro Thr Ser Ala Ala Lys Ala Pro Gly Leu Ile Pro Lys
             75              80              85

Leu Asp Thr Ala Tyr Asp Val Ala Tyr Lys Ala Ala Glu Ala His Pro
         90              95             100

Arg Gly Gln Val Arg Arg Leu Arg His Cys Pro His Arg Ser Leu Arg
        105             110             115

Val Ile Ala Gly Ala Leu Glu Val His Ala Val Lys Pro Ala Thr Glu
120             125             130             135

Glu Val Leu Ala Ala Lys Ile Pro Thr Gly Glu Leu Gln Ile Val Asp
             140             145             150

Lys Ile Asp Ala Ala Phe Lys Ile Ala Ala Thr Ala Ala Asn Ala Ala
             155             160             165

Pro Thr Asn Asp Lys Phe Thr Val Phe Glu Ser Ala Phe Asn Lys Ala
         170             175             180

Leu Asn Glu Cys Thr Gly Gly Ala Met Arg Pro Thr Ser Ser Ser Pro
         185             190             195

Pro Ser Arg Pro Arg Ser Ser Arg Pro Thr Pro Pro Ser Pro Ala
200             205             210             215

Ala Pro Glu Val Lys Tyr Ala Val Phe Glu Ala Ala Leu Thr Lys Ala
             220             225             230

Ile Thr Ala Met Thr Gln Ala Gln Lys Ala Gly Lys Pro Ala Ala Ala
             235             240             245

Ala Ala Thr Ala Ala Ala Thr Val Ala Thr Ala Ala Thr Ala Ala
         250             255             260

Ala Val Leu Pro Pro Leu Leu Val Val Gln Ser Leu Ile Ser Leu
265             270             275

Leu Ile Tyr Tyr
280
```

<210> SEQ ID NO 3

<211> LENGTH: 756
<212> TYPE: DNA
<213> ORGANISM: Lolium perenne
<220> FEATURE:
<221> NAME/KEY: CDS
<222> LOCATION: (3)..(437)

<400> SEQUENCE: 3

```
ac aat gag gag cct atc gca ccc tac cac ttc gac ctc tcg ggc cac        47
   Asn Glu Glu Pro Ile Ala Pro Tyr His Phe Asp Leu Ser Gly His
    1               5                  10                  15 gca ttc ggg tcc atg gcg aag aag ggc gag gag cag aag ctc cgc agc       95
Ala Phe Gly Ser Met Ala Lys Lys Gly Glu Glu Gln Lys Leu Arg Ser
                 20                  25                  30 gcc ggc gag ctg gag ctc cag ttc agg cgg gtc aag tgc aag tac ccg      143
Ala Gly Glu Leu Glu Leu Gln Phe Arg Arg Val Lys Cys Lys Tyr Pro
             35                  40                  45 gac ggc acc aag ccg aca ttc cac gtc gag aag ggt tcc aac ccc aac      191
Asp Gly Thr Lys Pro Thr Phe His Val Glu Lys Gly Ser Asn Pro Asn
         50                  55                  60 tac ctg gct att ctg gtg aag tac gtc gac ggc gac ggc gac gtg gtg      239
Tyr Leu Ala Ile Leu Val Lys Tyr Val Asp Gly Asp Gly Asp Val Val
 65                  70                  75 gcc gtg gac atc aag gag aag ggc aag gat aag tgg atc gag ctc aag      287
Ala Val Asp Ile Lys Glu Lys Gly Lys Asp Lys Trp Ile Glu Leu Lys
 80                  85                  90                  95 gag tcg tgg gga gca gtc tgg agg atc gac acc ccc gat aag ctg acg      335
Glu Ser Trp Gly Ala Val Trp Arg Ile Asp Thr Pro Asp Lys Leu Thr
                100                 105                 110 ggc cca ttc acc gtc cgc tac acc acc gag ggc ggc acc aaa tcc gaa      383
Gly Pro Phe Thr Val Arg Tyr Thr Thr Glu Gly Gly Thr Lys Ser Glu
            115                 120                 125 gtc gag gat gtc att cct gag ggc tgg aag gcc gac acc tcc tac tcg      431
Val Glu Asp Val Ile Pro Glu Gly Trp Lys Ala Asp Thr Ser Tyr Ser
        130                 135                 140 gcc aag tgagcaagaa gtggagtgat cttcttccaa tcagcttaat tttgactcaa       487
Ala Lys
    145 gatctcaaat aatccagccg cacatatata cgaggcggtg agacatacaa gctcctccat    547 gagtatattc attcatgccg tatagagagg agaaagatgc ctgaataaga gtttgaggtc    607 gacaccttgt gagaagtgta tataggagga acccaatctg gctccatctt tctttgctcg    667 cacggtgtac tgctaaggtt atcttctaac aggccagatt aacctactat ctaatatatg    727 caacgtatgg tcattttccc taaaaaaaa                                      756
```

<210> SEQ ID NO 4
<211> LENGTH: 145
<212> TYPE: PRT
<213> ORGANISM: Lolium perenne

<400> SEQUENCE: 4

```
Asn Glu Glu Pro Ile Ala Pro Tyr His Phe Asp Leu Ser Gly His Ala
 1               5                  10                  15

Phe Gly Ser Met Ala Lys Lys Gly Glu Glu Gln Lys Leu Arg Ser Ala
             20                  25                  30

Gly Glu Leu Glu Leu Gln Phe Arg Arg Val Lys Cys Lys Tyr Pro Asp
         35                  40                  45

Gly Thr Lys Pro Thr Phe His Val Glu Lys Gly Ser Asn Pro Asn Tyr
     50                  55                  60
```

```
Leu Ala Ile Leu Val Lys Tyr Val Asp Gly Asp Gly Asp Val Val Ala
 65                  70                  75                  80

Val Asp Ile Lys Glu Lys Gly Lys Asp Lys Trp Ile Glu Leu Lys Glu
                 85                  90                  95

Ser Trp Gly Ala Val Trp Arg Ile Asp Thr Pro Asp Lys Leu Thr Gly
            100                 105                 110

Pro Phe Thr Val Arg Tyr Thr Thr Glu Gly Gly Thr Lys Ser Glu Val
        115                 120                 125

Glu Asp Val Ile Pro Glu Gly Trp Lys Ala Asp Thr Ser Tyr Ser Ala
    130                 135                 140

Lys
145

<210> SEQ ID NO 5
<211> LENGTH: 810
<212> TYPE: DNA
<213> ORGANISM: Lolium perenne
<220> FEATURE:
<221> NAME/KEY: mat_peptide
<222> LOCATION: (85)..(804)
<221> NAME/KEY: CDS
<222> LOCATION: (16)..(804)

<400> SEQUENCE: 5
caaattcaag acaag atg gcg tcc tcc tcg tcg gtg ctc ctg gtg gtg gcg         51
              Met Ala Ser Ser Ser Ser Val Leu Leu Val Val Ala
                      -20                 -15 ctg ttc gcc gtg ttc ctg ggc agc gcg cat ggc atc gcg aag gta cca         99
Leu Phe Ala Val Phe Leu Gly Ser Ala His Gly Ile Ala Lys Val Pro
    -10                  -5                  -1   1                5 ccg ggc ccc aac atc acg gcc gag tac ggc gac aag tgg ctg gac gcg        147
Pro Gly Pro Asn Ile Thr Ala Glu Tyr Gly Asp Lys Trp Leu Asp Ala
                 10                  15                  20 aag agc acc tgg tat ggc aag ccg acc ggc gcc ggt ccc aag gac aac        195
Lys Ser Thr Trp Tyr Gly Lys Pro Thr Gly Ala Gly Pro Lys Asp Asn
             25                  30                  35 ggc gcg tgc ggg tac aag gac gtt gac aag gcg ccg ttc aac ggc            243
Gly Ala Cys Gly Tyr Lys Asp Val Asp Lys Ala Pro Phe Asn Gly
         40                  45                  50 atg acc ggc tgc ggc aac acc ccc atc ttc aag gac ggc cgt ggc tgc        291
Met Thr Gly Cys Gly Asn Thr Pro Ile Phe Lys Asp Gly Arg Gly Cys
     55                  60                  65 ggc tcc tgc ttc gag atc aag tgc acc aag ccc gag tcc tgc tcc ggc        339
Gly Ser Cys Phe Glu Ile Lys Cys Thr Lys Pro Glu Ser Cys Ser Gly
 70                  75                  80                  85 gag gct gtc acc gtc aca atc acc gac gac aac gag gag ccc atc gca        387
Glu Ala Val Thr Val Thr Ile Thr Asp Asp Asn Glu Glu Pro Ile Ala
                 90                  95                 100 ccc tac cat ttc gac ctc tcg ggc cac gcg ttc ggg tcc atg gcg aag        435
Pro Tyr His Phe Asp Leu Ser Gly His Ala Phe Gly Ser Met Ala Lys
            105                 110                 115 aag ggc gag gag cag aag ctc cgc agc gcc ggc gag ctg gag ctc cag        483
Lys Gly Glu Glu Gln Lys Leu Arg Ser Ala Gly Glu Leu Glu Leu Gln
        120                 125                 130 ttc agg cgg gtc aag tgc aag tac ccg gac ggc acc aag ccg aca ttc        531
Phe Arg Arg Val Lys Cys Lys Tyr Pro Asp Gly Thr Lys Pro Thr Phe
    135                 140                 145 cac gtc gag aag gct tcc aac ccc aac tac ctc gct att ctg gtg aag        579
His Val Glu Lys Ala Ser Asn Pro Asn Tyr Leu Ala Ile Leu Val Lys
150                 155                 160                 165
```

-continued

| | | | | | | | | | | | | | | |
|---|---|---|---|---|---|---|---|---|---|---|---|---|---|---|
| tac | gtc | gac | ggc | gac | ggt | gac | gtg | gtg | gcg | gtg | gac | atc | aag | gag | aag | 627 |
| Tyr | Val | Asp | Gly | Asp | Gly | Asp | Val | Val | Ala | Val | Asp | Ile | Lys | Glu | Lys |
| | | | 170 | | | | 175 | | | | | 180 | | | |

| ggc | aag | gat | aag | tgg | atc | gag | ctc | aag | gag | tcg | tgg | gga | gca | gtc | tgg | 675 |
| Gly | Lys | Asp | Lys | Trp | Ile | Glu | Leu | Lys | Glu | Ser | Trp | Gly | Ala | Val | Trp |
| | | | 185 | | | | | 190 | | | | | 195 | | |

| agg | atc | gac | acc | ccc | gat | aag | ctg | acg | ggc | cca | ttc | acc | gtc | cgc | tac | 723 |
| Arg | Ile | Asp | Thr | Pro | Asp | Lys | Leu | Thr | Gly | Pro | Phe | Thr | Val | Arg | Tyr |
| | 200 | | | | | 205 | | | | | 210 | | | | |

| acc | acc | gag | ggc | ggc | acc | aaa | tcc | gaa | gtc | gag | gat | gtc | atc | cct | gag | 771 |
| Thr | Thr | Glu | Gly | Gly | Thr | Lys | Ser | Glu | Val | Glu | Asp | Val | Ile | Pro | Glu |
| | 215 | | | | 220 | | | | | 225 | | | | | |

| ggc | tgg | aag | gcc | gac | acc | tcc | tac | tcg | gcc | aag | tgagca | | | | | 810 |
| Gly | Trp | Lys | Ala | Asp | Thr | Ser | Tyr | Ser | Ala | Lys |
| 230 | | | | 235 | | | | | 240 | |

<210> SEQ ID NO 6
<211> LENGTH: 263
<212> TYPE: PRT
<213> ORGANISM: Lolium perenne

<400> SEQUENCE: 6

Met Ala Ser Ser Ser Val Leu Leu Val Val Ala Leu Phe Ala Val
            -20            -15            -10

Phe Leu Gly Ser Ala His Gly Ile Ala Lys Val Pro Pro Gly Pro Asn
      -5            -1  1            5

Ile Thr Ala Glu Tyr Gly Asp Lys Trp Leu Asp Ala Lys Ser Thr Trp
10                  15                  20                  25

Tyr Gly Lys Pro Thr Gly Ala Gly Pro Lys Asp Asn Gly Gly Ala Cys
                30                  35                  40

Gly Tyr Lys Asp Val Asp Lys Ala Pro Phe Asn Gly Met Thr Gly Cys
            45                  50                  55

Gly Asn Thr Pro Ile Phe Lys Asp Gly Arg Gly Cys Gly Ser Cys Phe
        60                  65                  70

Glu Ile Lys Cys Thr Lys Pro Glu Ser Cys Ser Gly Glu Ala Val Thr
75                  80                  85

Val Thr Ile Thr Asp Asp Asn Glu Glu Pro Ile Ala Pro Tyr His Phe
90                  95                  100                 105

Asp Leu Ser Gly His Ala Phe Gly Ser Met Ala Lys Lys Gly Glu Glu
                110                 115                 120

Gln Lys Leu Arg Ser Ala Gly Glu Leu Glu Leu Gln Phe Arg Arg Val
            125                 130                 135

Lys Cys Lys Tyr Pro Asp Gly Thr Lys Pro Thr Phe His Val Glu Lys
        140                 145                 150

Ala Ser Asn Pro Asn Tyr Leu Ala Ile Leu Val Lys Tyr Val Asp Gly
    155                 160                 165

Asp Gly Asp Val Val Ala Val Asp Ile Lys Glu Lys Gly Lys Asp Lys
170                 175                 180                 185

Trp Ile Glu Leu Lys Glu Ser Trp Gly Ala Val Trp Arg Ile Asp Thr
                190                 195                 200

Pro Asp Lys Leu Thr Gly Pro Phe Thr Val Arg Tyr Thr Thr Glu Gly
            205                 210                 215

Gly Thr Lys Ser Glu Val Glu Asp Val Ile Pro Glu Gly Trp Lys Ala
        220                 225                 230

Asp Thr Ser Tyr Ser Ala Lys
    235                 240

-continued

<210> SEQ ID NO 7
<211> LENGTH: 30
<212> TYPE: DNA
<213> ORGANISM: Lolium perenne

<400> SEQUENCE: 7
gggtctagag gtaccgtccg atcgatcatt                                    30

<210> SEQ ID NO 8
<211> LENGTH: 13
<212> TYPE: DNA
<213> ORGANISM: Lolium perenne

<400> SEQUENCE: 8
aatgatcgat gct                                                      13

<210> SEQ ID NO 9
<211> LENGTH: 20
<212> TYPE: DNA
<213> ORGANISM: Lolium perenne

<400> SEQUENCE: 9
gggtctagag gtaccgtccg                                               20

<210> SEQ ID NO 10
<211> LENGTH: 26
<212> TYPE: DNA
<213> ORGANISM: Lolium perenne

<400> SEQUENCE: 10
ccctgcagat tatttgagat cttgag                                        26

<210> SEQ ID NO 11
<211> LENGTH: 29
<212> TYPE: DNA
<213> ORGANISM: Lolium perenne

<400> SEQUENCE: 11
ccctgcagtc atgctcactt ggccgagta                                     29

<210> SEQ ID NO 12
<211> LENGTH: 19
<212> TYPE: DNA
<213> ORGANISM: Lolium perenne

<400> SEQUENCE: 12
gagtacggcg acaagtggc                                                19

<210> SEQ ID NO 13
<211> LENGTH: 18
<212> TYPE: DNA
<213> ORGANISM: Lolium perenne

<400> SEQUENCE: 13
ttcgagatca agtgcacc                                                 18

<210> SEQ ID NO 14
<211> LENGTH: 16
<212> TYPE: DNA
<213> ORGANISM: Lolium perenne

<400> SEQUENCE: 14
gtgacagcct cgccgg                                                   16

```
<210> SEQ ID NO 15
<211> LENGTH: 24
<212> TYPE: DNA
<213> ORGANISM: Lolium perenne

<400> SEQUENCE: 15
gggaattcca tggcgaagaa gggc                                          24

<210> SEQ ID NO 16
<211> LENGTH: 16
<212> TYPE: DNA
<213> ORGANISM: Lolium perenne

<400> SEQUENCE: 16
gtgccgtccg ggtact                                                   16

<210> SEQ ID NO 17
<211> LENGTH: 16
<212> TYPE: DNA
<213> ORGANISM: Lolium perenne

<400> SEQUENCE: 17
ccgtcgacgt acttca                                                   16

<210> SEQ ID NO 18
<211> LENGTH: 19
<212> TYPE: DNA
<213> ORGANISM: Lolium perenne

<400> SEQUENCE: 18
ggagtcgtgg ggagcagtc                                                19

<210> SEQ ID NO 19
<211> LENGTH: 30
<212> TYPE: PRT
<213> ORGANISM: Lolium perenne
<220> FEATURE:
<223> OTHER INFORMATION: all occurrences of Xaa = any amino acid

<400> SEQUENCE: 19

Ile Ala Lys Val Xaa Pro Gly Xaa Xaa Ile Thr Ala Glu Tyr Gly Asp
 1               5                  10                  15

Lys Trp Leu Asp Ala Lys Ser Thr Trp Tyr Gly Lys Pro Thr
             20                  25                  30

<210> SEQ ID NO 20
<211> LENGTH: 30
<212> TYPE: PRT
<213> ORGANISM: Lolium perenne
<220> FEATURE:
<223> OTHER INFORMATION: at positions 6 and 8 Xaa = hydroxyproline
<223> OTHER INFORMATION: at positions 23 and 25-30 Xaa = any amino acid

<400> SEQUENCE: 20

Ile Ala Lys Val Pro Xaa Gly Xaa Trp Ile Thr Ala Glu Tyr Gly Asp
 1               5                  10                  15

Lys Trp Leu Asp Ala Lys Xaa Thr Xaa Xaa Xaa Xaa Xaa Xaa
             20                  25                  30

<210> SEQ ID NO 21
<211> LENGTH: 30
<212> TYPE: PRT
<213> ORGANISM: Lolium perenne
```

```
<400> SEQUENCE: 21

Ile Ala Lys Val Pro Pro Gly Pro Asn Ile Thr Ala Glu Tyr Gly Asp
1               5                   10                  15

Lys Trp Leu Asp Ala Lys Ser Thr Trp Tyr Gly Lys Pro Thr
            20                  25                  30

<210> SEQ ID NO 22
<211> LENGTH: 19
<212> TYPE: PRT
<213> ORGANISM: Lolium perenne
<220> FEATURE:
<223> OTHER INFORMATION: all occurrences of Xaa = any amino acid

<400> SEQUENCE: 22

Ala Asp Ala Gly Tyr Thr Pro Ala Ala Xaa Xaa Thr Pro Ala Thr Pro
1               5                   10                  15

Ala Xaa Thr

<210> SEQ ID NO 23
<211> LENGTH: 31
<212> TYPE: PRT
<213> ORGANISM: Lolium perenne

<400> SEQUENCE: 23

Ala Ala Pro Val Glu Phe Thr Val Glu Lys Gly Ser Asp Glu Lys Asn
1               5                   10                  15

Leu Ala Leu Ser Ile Lys Tyr Asn Lys Glu Gly Asp Ser Met Ala
            20                  25                  30

<210> SEQ ID NO 24
<211> LENGTH: 26
<212> TYPE: PRT
<213> ORGANISM: Lolium perenne

<400> SEQUENCE: 24

Ala Asp Ala Gly Tyr Thr Pro Ala Ala Ala Thr Pro Ala Thr Pro
1               5                   10                  15

Ala Ala Thr Pro Ala Gly Gly Trp Arg Glu
            20                  25

<210> SEQ ID NO 25
<211> LENGTH: 31
<212> TYPE: PRT
<213> ORGANISM: Lolium perenne
<220> FEATURE:
<223> OTHER INFORMATION: all occurrences of Xaa = any amino acid

<400> SEQUENCE: 25

Xaa Thr Lys Val Asp Leu Thr Val Glu Lys Gly Ser Asp Ala Lys Thr
1               5                   10                  15

Leu Val Leu Asn Ile Lys Tyr Thr Arg Pro Gly Asp Thr Leu Ala
            20                  25                  30
```